(12) United States Patent
Huang et al.

(10) Patent No.: US 10,704,057 B2
(45) Date of Patent: Jul. 7, 2020

(54) METHODS AND COMPOSITIONS FOR SELECTIVE REGULATION OF PROTEIN EXPRESSION

(71) Applicant: Monsanto Technology LLC, St. Louis, MO (US)

(72) Inventors: Jintai Huang, Chesterfield, MO (US); Youlin Qi, Chesterfield, MO (US); Heping Yang, St. Louis, MO (US); Yuanji Zhang, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 411 days.

(21) Appl. No.: 15/210,725

(22) Filed: Jul. 14, 2016

(65) Prior Publication Data
US 2017/0029841 A1    Feb. 2, 2017

Related U.S. Application Data

(60) Provisional application No. 62/195,546, filed on Jul. 22, 2015.

(51) Int. Cl.
*C12N 15/82* (2006.01)
*C12N 9/10* (2006.01)

(52) U.S. Cl.
CPC ....... *C12N 15/8275* (2013.01); *C12N 9/1092* (2013.01); *C12N 15/8218* (2013.01); *C12N 15/8231* (2013.01); *C12N 15/8274* (2013.01); *C12N 15/8289* (2013.01); *C12Y 205/01019* (2013.01)

(58) Field of Classification Search
None
See application file for complete search history.

(56) References Cited

U.S. PATENT DOCUMENTS

| | | | |
|---|---|---|---|
| 5,583,210 A | 12/1996 | Neill et al. | |
| 6,072,102 A | 6/2000 | Cigan et al. | |
| 6,646,186 B1 | 11/2003 | Stine et al. | |
| 7,230,168 B2 | 6/2007 | Huang et al. | |
| 7,355,096 B2 | 4/2008 | Spangenberg et al. | |
| 9,139,838 B2 * | 9/2015 | Huang | C12N 15/8289 |
| 2001/0023501 A1 | 9/2001 | Johal et al. | |
| 2002/0062499 A1 | 5/2002 | Conner et al. | |
| 2007/0199095 A1 | 8/2007 | Edwards et al. | |
| 2007/0209085 A1 | 9/2007 | Wu et al. | |
| 2011/0035838 A1 | 2/2011 | Lutfiyya et al. | |
| 2011/0126310 A1 | 5/2011 | Feng et al. | |
| 2011/0150832 A1 | 6/2011 | Nemunaitis et al. | |
| 2011/0167513 A1 | 7/2011 | Gils | |
| 2011/0271399 A1 | 11/2011 | Cerny et al. | |
| 2013/0007908 A1 * | 1/2013 | Huang | C12N 15/8289 |
| | | | 800/272 |
| 2018/0030474 A1 | 2/2018 | Huang et al. | |

FOREIGN PATENT DOCUMENTS

| | | |
|---|---|---|
| CL | 1891-1995 | 7/1996 |
| CL | 1704-2000 | 6/2001 |
| CL | 1652-2006 | 2/2007 |
| EA | 6761 B1 | 4/2006 |
| RU | 2380411 C2 | 1/2010 |
| WO | WO 1999/046396 | 9/1999 |
| WO | WO 2001/073087 | 10/2001 |
| WO | WO 2002/078427 | 10/2002 |
| WO | WO 2006/014678 | 2/2006 |
| WO | WO 2007/047016 | 4/2007 |
| WO | 2009091518 A2 | 7/2009 |
| WO | WO 2009/085982 | 7/2009 |
| WO | WO 2010/099084 | 9/2010 |

OTHER PUBLICATIONS

U.S. Appl. No. 15/726,363, filed Oct. 5, 2017, Huang et al.
USPTO: Non-Final Office Action regarding U.S. Appl. No. 15/726,363, dated Nov. 16, 2018.
Omidvar et al., "Identification of miRNAs with potential roles in regulation of anther development and male-sterility in 7B-1 male-sterile tomato mutant," BMC Genomics 16:878, 2015.
Grant-Downton et al., "Emerging Roles for Non-Coding RNAs in Male Reproductive Development in Flowering Plants," Biomolecules 2:608-621, 2012.
Li et al., "Analysis of small RNAs revealed differential expressions during pollen and embryo sac development in autotetraploid rice," BMC Genomics 18:129, 2017.
Response to Non-Final Office Action regarding U.S. Appl. No. 15/726,363, dated Feb. 19, 2019.
Office Action regarding Russian Application No. 2014103436, dated Dec. 26, 2017.
Tarantul V.Z. Biotechnological definition dictionary Russian-English, 2009, Moscow, sheets 936 (p. 396).
Chellappan et al., "siRNAs from miRNA sites mediate DNA methylation of target genes," *Nucleic Acids Research* 38:6883-6894, 2010.
Office Action regarding Chilean Application No. 201600869, dated Jan. 10, 2018.
GenBank Accession No. EU974548, dated Dec. 5, 2008.
Response to Non-Final Office Action regarding U.S. Appl. No. 14/720,052, dated Jun. 5, 2017.
USPTO: Notice of Allowance regarding U.S. Appl. No. 14/720,052, dated Jul. 6, 2017.
GenBank Accession No. BZ797057.1, dated Mar. 17, 2003.
Wang et al., "Development and validation of vectors containing multiple siRNA expression cassettes for maximizing the efficiency of gene silencing," *BMC Biotechnology* 6(50):1-7, 2006.
Zhai et al., "Spatiotemporally dynamic, cell-type—dependent premeiotic and meiotic phasiRNAs in maize anthers," *Proc Natl Acad Sci U S A*, 112:3146-3151, 2015.

(Continued)

*Primary Examiner* — Stephen Uyeno
(74) *Attorney, Agent, or Firm* — Dentons US LLP; Pamela Sisson

(57) ABSTRACT

The invention provides novel recombinant DNA molecules, compositions, and methods for selectively regulating the expression of a transcribable polynucleotide molecule or recombinant protein in a male reproductive tissue of a transgenic plant. The invention also provides transgenic plants, plant cells, plant parts, seeds, and commodity products comprising such DNA molecules and compositions.

21 Claims, 4 Drawing Sheets

Specification includes a Sequence Listing.

(56) References Cited

OTHER PUBLICATIONS

International Search Report and Written Opinion regarding International Application No. PCT/US2016/042217, dated Oct. 11, 2016.
European Extended Search Report regarding European Application No. 16828263, dated Apr. 17, 2019.
Yang et al., "Endogenous tassel-specific small RNAs-mediated RNA interference enables a novel glyphosate-inducible mail sterility system for commercial production of hybrid seed in Zea mays L.," PLoSOne 13(8):e0202921, 2018.
USPTO: Non-Final Office Action regarding U.S. Appl. No. 15/726,363, dated Apr. 30, 2019.
Chuck et al., "The heterochronic maize mutant Corngrass1 results from overexpression of a tandem microRNA," Nature Genetics 39(4):544-549, 2007.
Howe et al., "Glyphosate as a selective agent for the production of fertile transgenic maize (Zea mays L.) plants," Molecular Breeding 10:153-164, 2002.
Response to Non-Final Office Action regarding U.S. Appl. No. 15/726,363, dated Jul. 19, 2019.
Brazil Office Action regarding Brazilian Application No. BR112013033972-1, dated Aug. 6, 2019.
Johnson et al., "CSRDB: a small RNA integrated database and browser resource for cereals" Nucleic Acid Research D1-D5, 2006.
Nobuta et al., "Distinct size distribution of endogeneous siRNAs in maize: Evidence from deep sequencing in the mop1-1 mutant" PNAS 105(39):14958-14963, 2008.
Simon et al., "Small RNA-mediated epigenetic modifications in plants," Current Opinion in Plant Biology 14 (2):148-155, 2011.
Response to Final Office Action regarding U.S. Appl. No. 15/726,363, dated Nov. 7, 2019.
USPTO: Advisory Action regarding U.S. Appl. No. 15/726,363 dated Dec. 10, 2019.
Supplemental Response to Final Office Action regarding U.S. Appl. No. 15/726,363, dated Jan. 2, 2020.
USPTO: Notice of Allowance regarding U.S. Appl. No. 15/726,363, dated Feb. 12, 2020.
USPTO: Final Office Action regarding U.S. Appl. No. 15/726,363, dated Sep. 3, 2019.
U.S. Appl. No. 16/845,907, filed Apr. 10, 2020, Huang et al.
Colombia Office Action regarding Application No. NC2018/0000499, dated Feb. 20, 2020.

\* cited by examiner

METHODS AND COMPOSITIONS FOR SELECTIVE REGULATION OF PROTEIN EXPRESSION

CROSS-REFERENCE TO RELATED APPLICATIONS

This application claims the benefit of U.S. Provisional Application No. 62/195,546, filed on Jul. 22, 2015, herein incorporated by reference in its entirety.

INCORPORATION OF SEQUENCE LISTINGS

The sequence listing that is contained in the file named "MONS392US_ST25.txt", which is 26.3 kilobytes (measured in operating system MS-Windows), created on Jun. 28, 2016, is filed herewith and incorporated herein by reference.

BACKGROUND OF THE INVENTION

Field of the Invention

The invention relates generally to the fields of agriculture, plant breeding, and molecular biology. More specifically, the invention relates to methods and compositions for selectively regulating protein expression in the male reproductive tissue of transgenic plants and uses thereof.

Description of Related Art

Hybrid seed is produced by hybridization or cross-fertilization of closely related plants and can be grown into progeny hybrid plants possessing a desirable combination of traits not possessed by either parent plant. Hybrid plants can display superior agronomic characteristics such as improvement of plant size, yield, nutritional composition, disease resistance, herbicide tolerance, stress tolerance, climatic adaptation, and other desirable traits. Efficient hybrid seed production requires that a plant's own pollen not be permitted to self-fertilize the plant. A major limitation in the production of hybrid seed for many crops is the lack of simple, reliable, and economical methods of making plants male-sterile and incapable of self-fertilization.

In hybrid seed production, pollen production and pollen shed may be prevented in a female parent plant in order to facilitate cross-pollination of the female rather than self-pollination. Such prevention may be achieved by, for example, manual removal of the pollen-containing structures (for example, by manual or mechanical detasseling in maize), use of a genetic means of pollination control (for example, by using cytoplasmic male-sterile or nuclear male-sterile technology), use of a chemical agent, or any combination of these. This can be a labor-intensive and therefore expensive process. In maize, for example, detasseling is typically done in two steps: machine detasseling followed by manual detasseling. Commercial production of hybrid seed using solely chemical gametocides is limited primarily by their general lack of selectivity for gametes and their effect on the other parts of the plant. Thus, methods for improving the efficiency of hybrid seed production are highly desirable.

BRIEF SUMMARY OF THE INVENTION

The invention relates generally to improvements to methods of selectively regulating protein expression in the male reproductive tissue of transgenic plants, recombinant DNA molecules useful in such methods, as well as transgenic plants, cells, and seeds containing such recombinant DNA molecules. The invention provides an improvement over the art by providing male tissue-specific siRNA (mts-siRNA) target elements capable of providing improved selective regulation of the expression of a protein encoded by a transcribable polynucleotide molecule and provides recombinant DNA molecules and compositions comprising such mts-siRNA target elements and methods of using such mts-siRNA target elements for inducing male sterility in transgenic plants for the production of hybrid seed.

In one aspect, the invention provides a recombinant DNA molecule comprising a mts-siRNA target element operably linked to a heterologous transcribable polynucleotide molecule. In one embodiment, the mts-siRNA target element is included within a 3' untranslated region operably linked to the heterologous transcribable polynucleotide molecule. In another embodiment, the mts-siRNA target element is located between the heterologous transcribable polynucleotide molecule and an operably linked polyadenylation sequence that is part of a 3' untranslated region. In one embodiment, the mts-siRNA target element comprises a sequence selected from the group consisting of SEQ ID NO: 1-16, 23-92, and complements thereof. In another embodiment, the heterologous transcribable polynucleotide molecule confers herbicide tolerance, for instance vegetative herbicide tolerance, to a plant. In a further embodiment, the heterologous transcribable polynucleotide molecule does not confer male reproductive herbicide tolerance to a plant. In another embodiment, the heterologous transcribable polynucleotide molecule is a glyphosate-tolerant 5-enolypyruvyl shikimate 3-phosphate synthase (EPSPS).

In another aspect, the invention provides a recombinant DNA construct comprising a mts-siRNA target element of the invention operably linked to a heterologous transcribable polynucleotide molecule.

In further aspect, the invention provides a method of producing a recombinant DNA molecule comprising operably linking at least one mts-siRNA target element to a heterologous transcribable polynucleotide molecule. In one embodiment, the mts-siRNA target element comprises a sequence selected from the group consisting of SEQ ID NO: 1-16, 23-92, and complements thereof.

In another aspect, the invention provides a transgenic plant comprising a mts-siRNA target element of the invention. In one embodiment, the transgenic plant comprises the mts-siRNA target element operably linked to a heterologous transcribable polynucleotide molecule. In a further embodiment, the mts-siRNA target element comprises a sequence selected from the group consisting of SEQ ID NO: 1-16, 23-92, and complements thereof. In yet another embodiment, the transgenic plant is produced by transforming a plant with a recombinant DNA molecule or DNA construct comprising at least one mts-siRNA target element operably linked to a heterologous transcribable polynucleotide molecule. In a further aspect, the invention provides a seed, cell, or part of such a transgenic plant. In one embodiment, the plant is a monocotyledonous plant. In another embodiment, the plant is a maize (*Zea mays*) plant.

In a further aspect, the invention also provides a method of selectively regulating the expression of a protein in a male reproductive tissue of a transgenic plant by expressing in the transgenic plant a recombinant DNA molecule that comprises a mts-siRNA target element operably linked to a heterologous transcribable polynucleotide molecule. In one embodiment, the mts-siRNA target element comprises a sequence selected from the group consisting of SEQ ID NO: 1-16, 23-92, and complements thereof. In another embodiment, the heterologous transcribable polynucleotide molecule confers herbicide tolerance, for instance vegetative herbicide tolerance, to a plant. In a further embodiment, the heterologous transcribable polynucleotide molecule does not confer male reproductive herbicide tolerance to a plant. In another embodiment, the heterologous transcribable polynucleotide molecule is a glyphosate-tolerant EPSPS.

In yet another aspect, the invention provides a method of inducing male sterility in a transgenic plant, including the step of applying herbicide to a transgenic plant that has in its genome a recombinant DNA molecule comprising a mts-siRNA target element operably linked to a heterologous transcribable polynucleotide molecule that confers tolerance to at least a first herbicide to the transgenic plant, wherein the herbicide is applied prior to or concurrently with the development of the male reproductive tissue of the transgenic plant, thereby inducing male-sterility in the transgenic plant. In one embodiment, the heterologous transcribable polynucleotide molecule confers vegetative herbicide tolerance, but does not confer male reproductive herbicide tolerance to the transgenic plant. In another embodiment, the transgenic plant is a maize plant. In a further embodiment, the herbicide application prevents at least pollen development, pollen shed, or anther extrusion in the treated transgenic plant. In another embodiment, the developmental stage of the male reproductive tissue during which herbicide is applied is a stage selected from the group consisting of the V4, V5, V6, V7, V8, V9, V10, V11, V12, V13, and V14 stage of maize plant development. In another embodiment, the herbicide is selected from the group consisting of acetyl coenzyme A carboxylase (ACCase) inhibitors, acetolactate synthase (ALS) inhibitors, photosystem II (PSII) inhibitors, protoporphyrinogen oxidase (PPO) inhibitors, 4-hydroxyphenyl dioxygenase (HPPD) inhibitors, 5-enolypyruvyl shikimate 3-phosphate synthase (EPSPS) inhibitors, glutamine synthetase (GS) inhibitors, and synthetic auxins. In another embodiment, the herbicide is glyphosate and the heterologous transcribable polynucleotide encodes a glyphosate-tolerant EPSPS.

In one aspect, the invention also provides a method of producing hybrid seed comprising applying an effective amount of an herbicide to a transgenic plant comprising in its genome a recombinant DNA molecule comprising a mts-siRNA target element operably linked to a heterologous transcribable polynucleotide molecule, wherein the herbicide is applied prior to or concurrently with the development of the male reproductive tissue of the transgenic plant, thereby inducing male sterility in the transgenic plant; fertilizing the transgenic plant with pollen from a second plant; and allowing hybrid seed to form from the transgenic plant. In one embodiment, the transgenic plant is maize. In another embodiment, the herbicide is glyphosate and the heterologous transcribable polynucleotide molecule is a glyphosate-tolerant EPSPS. In another embodiment, the glyphosate is applied concurrently with development at an effective amount of about 0.125 pounds acid equivalent per acre to about 8 pounds acid equivalent per acre. In another aspect, the invention provides hybrid seed produced by such a method. In one embodiment, the hybrid seed comprises the recombinant DNA molecule.

Other specific embodiments of the invention are disclosed in the following detailed description. Throughout this specification and the claims, unless the context requires otherwise, the word "comprise" and its variations, such as "comprises" and "comprising", will be understood to imply the inclusion of a stated integer, element, or step or group of integers, elements, or steps, but not the exclusion of any other integer, element, or step or group of integers, elements, or steps.

BRIEF DESCRIPTION OF THE SEQUENCES

Figure 1:
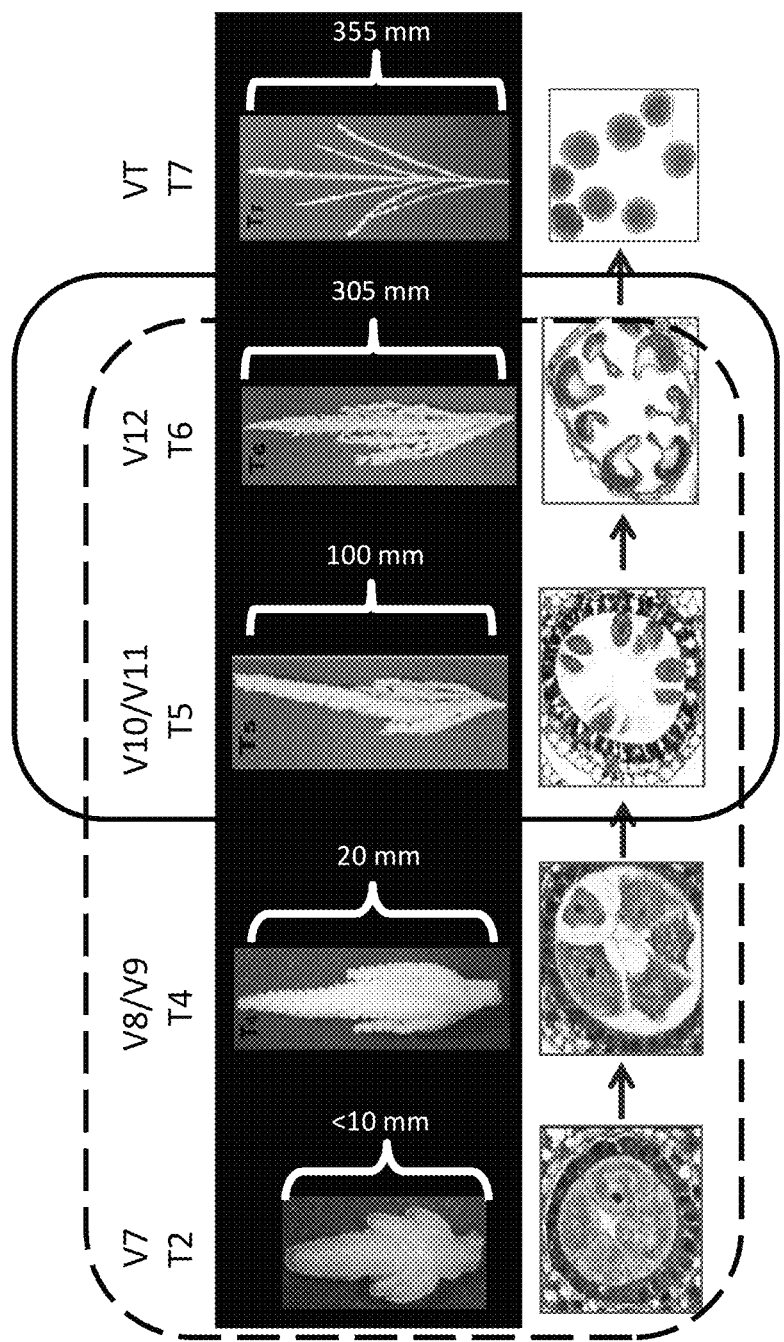
FIG. 1. Illustration of tassel developmental stages V7 at T2, V8/V9 at T4, V10/V11 at T5, V12 at T6, and VT at T7 showing tassel size and morphology with the lower panel photographs of cross-sections of anthers showing the pollen developmental stage. The stages previously (V10/V11 and V12) used in the art for isolating small RNA molecules for identification of mts-siRNA molecules are indicated by a box with solid line; the stages (V7, V8/V9, V10/V11 and V12) described herein for isolating small RNA molecules are indicated by a box with dashed line.

SEQ ID NO: 1—A mts-siRNA target element sequence having 95% sequence identity to nucleotide positions 1429 to 1628 of the cDNA sequence provided herein as SEQ ID NO: 17.

SEQ ID NO: 2—A mts-siRNA target element sequence having 95% sequence identity to nucleotide positions 1429 to 1628 of the cDNA sequence provided herein as SEQ ID NO: 17 and having a single nucleotide change (T69A) relative to SEQ ID NO: 1.

SEQ ID NO: 3—A mts-siRNA target element sequence that corresponds to nucleotide positions 239 to 433 of the cDNA sequence provided herein as SEQ ID NO: 18.

SEQ ID NO: 4—A mts-siRNA target element sequence that corresponds to nucleotide positions 477 to 697 of the cDNA sequence provided herein as SEQ ID NO: 18.

SEQ ID NO: 5—A mts-siRNA target element sequence that corresponds to nucleotide positions 239 to 433 of the cDNA sequence provided herein as SEQ ID NO: 19.

SEQ ID NO: 6—A mts-siRNA target element sequence that corresponds to nucleotide positions 370 to 477 of the cDNA sequence provided herein as SEQ ID NO: 19.

SEQ ID NO: 7—A mts-siRNA target element sequence that corresponds to nucleotide positions 1357 to 1562 of the cDNA sequence provided herein as SEQ ID NO: 20.

SEQ ID NO: 8—A mts-siRNA target element sequence that corresponds to nucleotide positions 247 to 441 of the cDNA sequence provided herein as SEQ ID NO: 21.

SEQ ID NO: 9—The reverse complement of a mts-siRNA target element sequence having 99% sequence identity to nucleotide positions 191 to 490 of the cDNA sequence provided herein as SEQ ID NO: 22 with three nucleotide mismatches (C314A, A350G, and G408A).

SEQ ID NOs: 10-16—Recombinant mts-siRNA target element sequences.

SEQ ID NO: 17—cDNA sequence containing at least one mts-siRNA target sequence rich region. Contains the mts-siRNA target element sequences represented by SEQ ID NO: 1 and SEQ ID NO: 2 and aligns to mts-siRNA sequences SEQ ID NOs: 23-31.

SEQ ID NO: 18—cDNA sequence containing at least one mts-siRNA target sequence rich region. Contains the mts-siRNA target element sequences represented by SEQ ID NO: 3 and SEQ ID NO: 4 and aligns to mts-siRNA sequences SEQ ID NOs: 32-42.

SEQ ID NO: 19—cDNA sequence containing at least one mts-siRNA target sequence rich region. Contains the mts-siRNA target element sequences represented by SEQ ID NO: 5 and SEQ ID NO: 6 and aligns to mts-siRNA sequences SEQ ID NOs: 43-52.

SEQ ID NO: 20—cDNA sequence containing at least one mts-siRNA target sequence rich region. Contains the mts-siRNA target element sequence represented by SEQ ID NO: 7 and aligns to mts-siRNA sequences SEQ ID NOs: 53-60.

SEQ ID NO: 21—cDNA sequence containing at least one mts-siRNA target sequence rich region. Contains the mts-siRNA target element sequence represented by SEQ ID NO: 8 and aligns to mts-siRNA sequences SEQ ID NOs: 61-69.

SEQ ID NO: 22—cDNA sequence containing at least one mts-siRNA target sequence rich region. Contains the mts-siRNA target element sequence represented by SEQ ID NO: 9 and aligns to mts-siRNA sequences SEQ ID NOs: 70-87.

SEQ ID NO: 23-92—DNA sequences corresponding to the mts-siRNA sequences of the invention, which align to the cDNA sequences provided herein as SEQ ID NOs: 17-22.

DETAILED DESCRIPTION OF THE INVENTION

The invention provides recombinant DNA molecules, compositions and methods for selectively regulating protein expression, for instance expression of a heterologous transcribable polynucleotide molecule, in a male reproductive tissue of a transgenic plant and uses thereof. In one aspect, the invention provides a recombinant DNA molecule that includes a male tissue-specific small interfering RNA (mts-siRNA) target element operably linked to a heterologous transcribable polynucleotide. Such recombinant DNA molecules are useful for selectively regulating the expression of a heterologous transcribable polynucleotide in a male reproductive tissue of a transgenic plant. Nucleic acid sequences can be provided as DNA or as RNA, as specified; disclosure of one necessarily defines the other, as is known to one of ordinary skill in the art. Furthermore, disclosure of a given nucleic acid sequence necessarily defines and includes the complement of that sequence, as is known to one of ordinary skill in the art.

Small interfering RNA (siRNA) is a class of RNA molecules of about 18-26 nucleotides (nt) in length (for example, 18, 19, 20, 21, 22, 23, 24, 25, or 26 nt). A siRNA sequence may be represented using the RNA nucleotide sequence consisting of guanine (G), cytosine (C), adenine (A), and uracil (U) or using the equivalent DNA nucleotide sequence of guanine (G), cytosine (C), adenine (A), and thymine (T). siRNA functions within RNA-induced silencing complexes (RISCs) to trigger the sequence specific degradation of messenger RNA (mRNA), which results in the disruption of the gene expression and down-regulation of the protein encoded by the gene.

A "male tissue-specific siRNA" or "mts-siRNA" is a siRNA enriched or specifically expressed in the male reproductive tissue(s) (for example, male inflorescence) of a plant thus having a male tissue-specific expression pattern. Male tissue-specific siRNA have been identified in plants and can be detected using techniques known in the art, such as low molecular weight northern analysis. A "mts-siRNA sequence" is the nucleic acid sequence of an mts-siRNA. Exemplary mts-siRNA sequences in the form of the corresponding DNA sequence of the double stranded mts-siRNA molecule are provided herein as SEQ ID NO: 23-92.

Figure 3:
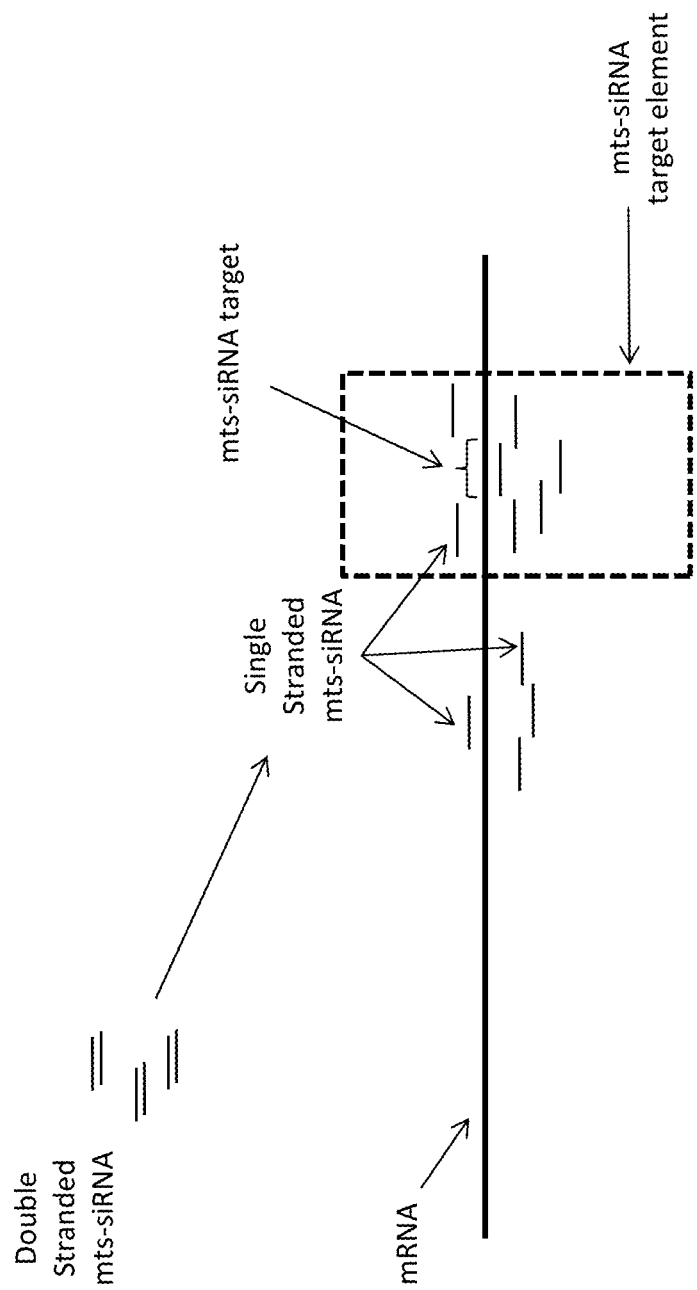
FIG. 3. Diagram illustrating double stranded mts-siRNA, single stranded mts-siRNA, mts-siRNA target sequence within a mRNA, and a region of mRNA with a high number of mts-siRNA target sequences useful as a mts-siRNA target element.
Figure 4:
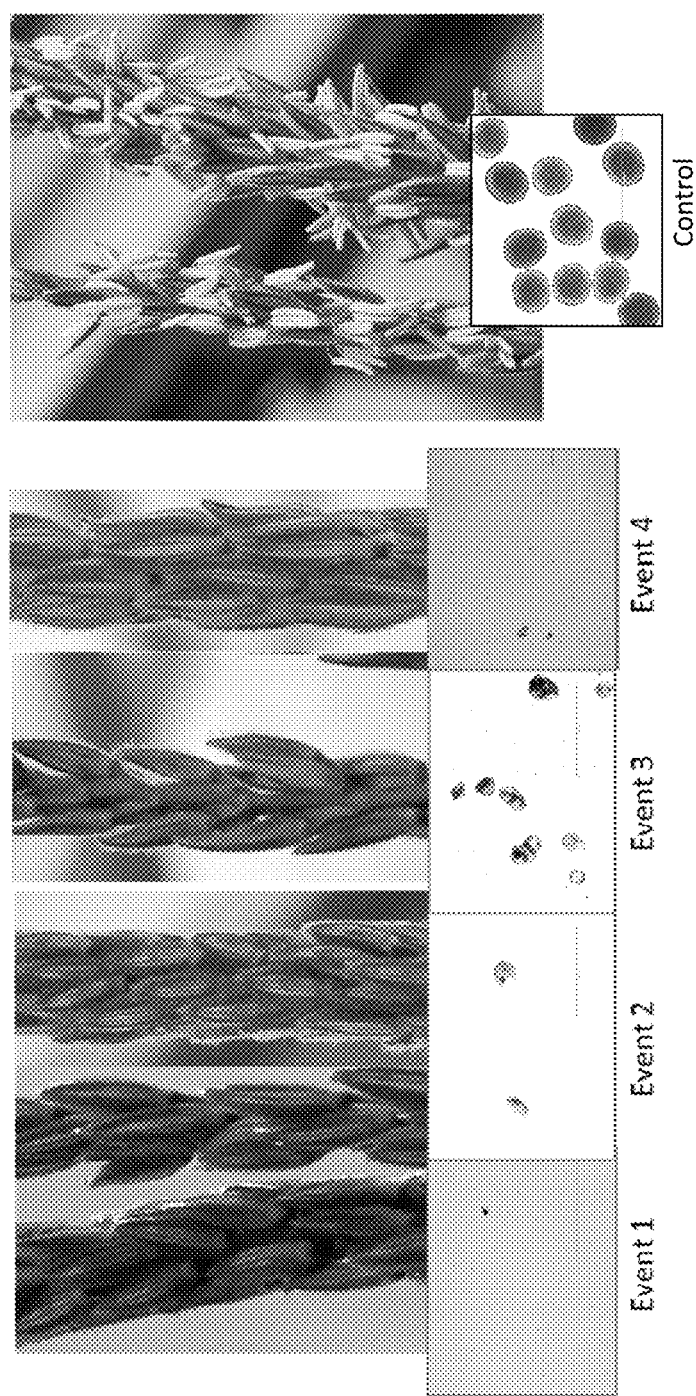
FIG. 4. Photograph of R0 maize tassel and pollen stained with Alexandar stain from double copy transgenic plants containing a recombinant DNA molecule comprising a transgene encoding a glyphosate-tolerant EPSPS protein operably linked to a mts-siRNA target element (SEQ ID NO: 2). Events 1 through 4 were sprayed with 0.75 lb ae/acre glyphosate herbicide at V5 followed by V8 stage and showed tassels with complete male sterility as defined by no anthesis and either nonviable pollen grains or no pollen grains detected in the anthers. Control plants did not receive a glyphosate application and demonstrated normal anthesis and pollen shedding and the microscopic observation detected normal pollen grains.

A DNA sequence that is complementary to a mts-siRNA sequence is referred to herein as an "mts-siRNA target". The mts-siRNA target is contained in the DNA sequence of a gene and is transcribed into the RNA sequence of the corresponding mRNA molecule. A single-strand of a double-stranded mts-siRNA molecule can then bind or hybridize under typical physiological conditions to the mts-siRNA target in the mRNA molecule. See FIG. 3. A nucleic acid sequence is complimentary to a mts-siRNA sequence if an alignment of the two nucleic acid sequences produces an exact match (with no mismatches i.e. complete complement), one mismatch, two mismatches, or three mismatches over the length of the mts-siRNA sequence. Complementary sequences can base-pair with each other according to the standard Watson-Crick complementarity rules (i e., guanine pairs with cytosine (G:C) and adenine pairs with either thymine (A:T) or uracil (A:U). A "mts-siRNA target sequence" is the nucleic acid sequence of an mts-siRNA target. Exemplary mts-siRNA target sequences are provided herein as SEQ ID NO: 23-92.

More than one mts-siRNA target can be clustered together or even overlap within a single DNA molecule. A DNA molecule comprising more than one mts-siRNA target is referred to herein as a "mts-siRNA target element". A mts-siRNA target element comprises at least two or more mts-siRNA targets within a 500 nucleotide sequence window. A mts-siRNA target element can be any length, such as about 30 nucleotides (nt), about 40 nt, about 50 nt, about 60 nt, about 70 nt, about 80 nt, about 90 nt, about 100 nt, about 150 nt, about 200 nt, about 250 nt, about 300 nt, about 350 nt, about 400 nt, about 450 nt, or about 500 nt. A "mts-siRNA target element sequence" is the nucleic acid sequence of an mts-siRNA target element. Exemplary mts-siRNA target element sequences are provided herein as SEQ ID NO: 1-16.

As used herein, a "recombinant" DNA molecule, polypeptide, protein, cell, or organism may be a non-naturally occurring or man-made creation using the tools of genetic engineering and as such is the product of human activity and would not otherwise normally occur in nature. A "recombinant DNA molecule" refers to a DNA molecule comprising a combination of DNA sequences or molecules that would not naturally occur together without human intervention. For instance, a recombinant DNA molecule may be a DNA molecule that is comprised of at least two DNA molecules heterologous with respect to each other, a DNA molecule that comprises a DNA sequence that deviates from DNA sequences that exist in nature, or a DNA molecule that has been incorporated into a host cell's DNA by genetic transformation. In one embodiment, a recombinant DNA molecule of the invention is a DNA molecule comprising a mts-siRNA target element operably linked to at least one transcribable polynucleotide molecule, for instance, where the transcribable polynucleotide molecule is heterologous to the mts-siRNA target element. As used herein a "recombinant" molecule or cell or organism may refer to a man-made.

As used herein, the term "heterologous" refers to the combination of two or more DNA molecules or proteins when such a combination is not normally found in nature or when such a combination is provided in an orientation or order that is different than that found in nature. For example, the two DNA molecules may be derived from different species or created synthetically and/or the two DNA molecules may be derived from different genes, e.g., different genes from the same species or the same genes from different species. In one example, a regulatory element or mts-siRNA target element may be heterologous with respect to an operably linked transcribable polynucleotide molecule if such a combination is not normally found in nature, i.e., the transcribable polynucleotide molecule does not naturally occur operably linked to the regulatory element or mts-siRNA target element. In one embodiment, such a heterologous combination may comprise a mts-siRNA target element that may be a plant-derived or chemically synthesized and may be operably linked to a transcribable polynucleotide molecule, such as a bacterial transgene encoding a protein for herbicide tolerance, such as a cp4-EPSPS (for instance as provided here as SEQ ID NO: 93). In addition, a particular sequence can be "heterologous" with respect to a cell or organism into which it is introduced (for example, a sequence that does not naturally occur in that particular cell or organism).

As used herein, the term "isolated" means separated from other molecules typically associated with it in its natural state. For example, an isolated DNA molecule is one that is present alone or in combination with other compositions, but is not in its natural genomic location or state. In one embodiment, the term "isolated" refers to a DNA molecule that is separated from the nucleic acids that normally flank the DNA molecule in its natural state. For example, an isolated DNA molecule may be a DNA molecule that is comprised of at least two DNA molecules heterologous with respect to each other. In another example, an isolated DNA molecule may be a DNA molecule that has been incorporated into a novel genomic location in a host cell by genetic transformation. Thus, a DNA molecule fused to or operably linked to one or more other DNA molecule(s) with which it would not be associated in nature, for example as the result of recombinant DNA or plant transformation techniques, is considered isolated herein. Such molecules are considered isolated even when integrated into the chromosome of a host cell or present in a nucleic acid solution with other DNA molecules.

The term "operably linked" refers to at least two nucleotide molecules arranged or linked in a manner so that one can affect the function of the other. The two nucleotide molecules can be part of a single contiguous nucleotide molecule and can be adjacent or separated. For example, a mts-siRNA target element may be operably linked with a transcribable polynucleotide molecule. In one embodiment, an operably linked mts-siRNA molecule can affect the transcription, translation, or expression of the transcribable polynucleotide molecule. For example, a mts-siRNA target element is operably linked to a transcribable polynucleotide molecule if, after transcription in male reproductive tissue cell, the presence of the mts-siRNA target element in the mRNA molecule results in the regulation of the expression of the transcribable polynucleotide molecule in the cell induced by the endogenous mts-siRNA and the RISC pathway. Operable linkage of the mts-siRNA target element and the transcribable polynucleotide molecule can be achieved, for example, through incorporation of a mts-siRNA target element adjacent to the transcribable polynucleotide molecule (such as located 5' or 3' to the transcribable polynucleotide molecule, but not necessarily in contiguous linkage), in or adjacent to an untranslated region (UTR) of the polynucleotide molecule (such as located in or next to the 5' UTR or the 3' UTR), and/or 3' to the transcribable polynucleotide molecule and 5' to the polyadenylation signal. In one embodiment, a mts-siRNA target element is located between the transcribable polynucleotide molecule and the polyadenylation sequence, that is 3' to and adjacent to the transcribable polynucleotide molecule. In another embodiment, a mts-siRNA target element is located between the stop codon of the transcribable polynucleotide molecule and the polyadenylation sequence. In another embodiment, a mts-siRNA target element is located within the 3' UTR sequence adjacent to the transcribable polynucleotide molecule.

Examples of the identification of mts-siRNA, mts-siRNA targets, and mts-siRNA target elements are provided herein and can be identified by methods known to those skilled in the art, for example through bioinformatic analysis of plant sRNA and cDNA libraries. In particular, mts-siRNA can be identified from sRNA libraries and sequenced. The identified mts-siRNA sequences can be compared to cDNA and/or genomic sequence collections to identify mts-siRNA targets and mts-siRNA target elements useful for developing recombinant DNA molecules and constructs as described herein.

In some embodiments, mts-siRNA target elements are created, synthesized, or modified in vitro. For instance, mts-siRNA target elements may be modified to contain more, fewer, or different mts-siRNA target sequences or to rearrange the relative position of one or more mts-siRNA target sequence(s). In some embodiments, such modification may be beneficial in increasing or decreasing the effect of the mts-siRNA target element. Methods for creation, synthesis, or in vitro modification of a mts-siRNA target element and for determining the optimal variation for the desired level of regulation are known by those of skill in the art. Exemplary recombinant mts-siRNA target elements can be created by combining the DNA sequences, or fragments thereof, of two or more mts-siRNA targets, two or more mts-siRNA target elements, two or more mts-siRNA target rich cDNA regions, or one or more mts-siRNA targets and fragments of two or more mts-siRNA target rich cDNA regions, such as by combining all or fragments of two or more of the mts-siRNA target elements provided herein as SEQ ID NO: 1-9, by combining two or more of the mts-siRNA sequences provided herein as SEQ ID NO: 23-92, or by combining all or fragments of two or more of the mts-siRNA target elements provided herein as SEQ ID NO: 1-9 with one or more of the mts-siRNA sequences provided herein as SEQ ID NO: 23-92. Such exemplary recombinant mts-siRNA target elements are provided herein as SEQ ID NO: 10-16.

The DNA sequence of the mts-siRNA target element can also be varied by incorporating 1-3 nucleotide mismatches in a mts-siRNA target sequence (relative to a given mts-siRNA sequence). In another embodiment, the present invention includes recombinant DNA molecules or mts-siRNA target elements having at least about 80% (percent) sequence identity, about 85% sequence identity, about 90% sequence identity, about 91% sequence identity, about 92% sequence identity, about 93% sequence identity, about 94% sequence identity, about 95% sequence identity, about 96% sequence identity, about 97% sequence identity, about 98% sequence identity, and about 99% sequence identity to any of the DNA molecules, mts-siRNA target elements (such as SEQ ID NOs: 1-9), recombinant mts-siRNA target elements (such as SEQ ID NOs: 10-16), or cDNA sequences (such as SEQ ID NOs: 17-22) of the present invention.

In another embodiment, the present invention provides fragments of a DNA molecule disclosed herein. Such fragments may be useful as mts-siRNA target elements or may be combined with other mts-siRNA target elements, mt-siRNA sequences, or fragments thereof for constructing recombinant mts-siRNA target elements, as described above. In specific embodiments, such fragments may comprise at least about 20, at least about 30, at least about 40, at least about 50, at least about 60, at least about 70, at least about 80, at least about 90, at least about 100, at least about 110, at least about 120, at least about 130, at least about 140, at least about 150, at least about 160, at least about 170, at least about 180, at least about 190, at least about 200, at least about 210, at least about 220, at least about 230, at least about 240, at least about 250, at least about 260, at least about 270, at least about 280, at least about 290, at least about 300, at least about 350, at least about 400, at least about 450, at least about 500 contiguous nucleotides, or longer, of a DNA molecule disclosed herein, such as a mts-siRNA target element or cDNA sequence as disclosed herein. Methods for producing such fragments from a starting DNA molecule are well known in the art.

The efficacy of the modifications, duplications, deletions, or rearrangements described herein on the desired expression aspects of a particular transcribable polynucleotide molecule may be tested empirically in stable and transient plant assays, such as those described in the working examples herein, so as to validate the results, which may vary depending upon the changes made and the goal of the change in the starting DNA molecule.

A mts-siRNA target and a mts-siRNA target element can function in either direction, meaning it is non-directional, and as such can be used in either the 5' to 3' orientation or in the 3' to 5' orientation in a recombinant DNA molecule or DNA construct.

As used herein, "expression of a transcribable polynucleotide molecule" or "expression of a protein" refers to the production of a protein from a transcribable polynucleotide molecule and the resulting transcript (mRNA) in a cell. The term "protein expression" therefore refers to any pattern of translation of a transcribed RNA molecule into a protein molecule. Protein expression may be characterized by its temporal, spatial, developmental, or morphological qualities, as well as by quantitative or qualitative indications. In one embodiment, recombinant DNA molecules of the invention can be used to selectively regulate expression of a protein or transcribable polynucleotide molecule in male reproductive tissues of a transgenic plant. In such an embodiment, expression of the recombinant DNA molecule in a transgenic plant may result in expression of an operably linked transcribable polynucleotide molecule in at least vegetative tissues but not in male reproductive tissues. In certain embodiments, such regulation of protein expression refers to suppressing or reducing; for example, suppressing or reducing the level of protein produced in a cell, for example through RNAi-mediated post-transcriptional gene regulation.

Selective regulation of protein expression as used herein refers to a reduction of protein production in a cell or tissue as compared to a reference cell or tissue by at least about 75%, at least about 80%, at least about 85%, at least about 90%, at least about 95%, at least about 99%, or 100% reduction (i.e. complete reduction). A reference cell or tissue can be, for example, a vegetative cell or tissue from the same or a similar transgenic plant expressing the protein or a cell or tissue from a transgenic plant having a similar transgene encoding the protein but lacking an operably linked mts-siRNA target element. Regulation of protein expression can be determined using any technique known to one skilled in the art, such as by directly measuring protein accumulation in a cell or tissue sample using a technique such as ELISA or western blot analysis, by measuring enzymatic activity of the protein, or by phenotypically determining protein expression. In one embodiment, selective regulation of protein expression refers to sufficient reduction in expression of a protein capable of conferring herbicide tolerance in the male tissue of a transgenic plant to result in a detectable phenotype of altered male fertility in a transgenic plant to which herbicide was applied as an induced sterility spray. The detection of altered male fertility in such a transgenic plant would therefore indicate the selective regulation of the protein expression.

As used herein, the term "transgene encoding a recombinant protein" or "transcribable polynucleotide molecule" refers to any nucleotide molecule capable of being transcribed into a RNA molecule, including but not limited to, those having a nucleotide sequence encoding a polypeptide sequence. Depending upon conditions, the nucleotide sequence may or may not be actually translated into a polypeptide molecule in a cell. The boundaries of a transgene or transcribable polynucleotide molecule are commonly delineated by a translation start codon at the 5'-terminus and a translation stop codon at the 3'-terminus.

The term "transgene" refers to a DNA molecule artificially incorporated into the genome of an organism or host cell, in the current or any prior generation of the organism or cell, as a result of human intervention, such as by plant transformation methods. As used herein, the term "transgenic" means comprising a transgene, for example a "transgenic plant" refers to a plant comprising a transgene in its genome and a "transgenic trait" refers to a characteristic or phenotype conveyed or conferred by the presence of a transgene incorporated into the plant genome. As a result of such genomic alteration, the transgenic plant is something distinctly different from the related wild-type plant and the transgenic trait is a trait not naturally found in the wild-type plant. Transgenic plants of the invention comprise the recombinant DNA molecule provided by the invention.

A transgene or transcribable polynucleotide molecule of the invention includes, but is not limited to, a transgene or transcribable polynucleotide molecule that provides a desirable characteristic associated with plant morphology, physiology, growth, development, yield, nutritional properties, disease resistance, pest resistance, herbicide tolerance, stress tolerance, environmental stress tolerance, or chemical tolerance. In one embodiment, a transcribable polynucleotide molecule of the invention encodes a protein that when expressed in a transgenic plant confers herbicide tolerance at least in a cell and/or tissue where the expressed protein occurs; selective regulation of the herbicide tolerance protein in male reproductive tissue of the transgenic plant in conjunction with timely application of the herbicide results in at least induced reduced male fertility or induced male sterility.

Such inducible male-sterility combined with vegetative herbicide tolerance can be used to increase the efficiency with which hybrid seed is produced, for example by eliminating or reducing the need to physically emasculate the maize plant used as a female in a given cross during hybrid seed production. Herbicide-inducible male-sterility systems have been described, for instance in U.S. Pat. Nos. 6,762, 344; 8,618,358; and U.S. Patent Publication 2013/0007908. Examples of herbicides useful in practicing the invention include, but are not limited to, acetyl coenzyme A carboxylase (ACCase) inhibitors (for example, fops and dims), acetolactate synthase (ALS) inhibitors (for example, sulfonylureas (SUs) and imidazolinones (IMIs)), photosystem II (PSII) inhibitors (for example, traiazines and phenyl ethers), protoporphyrinogen oxidase (PPO) inhibitors (for example, flumioxazsin and fomesafen), 4-hydroxyphenyl pyruvate dioxygenase (HPPD) inhibitors (for example, isoxaflutole and triketones such as mesotrione), 5-enolypyruvyl shikimate 3-phosphate synthase (EPSPS) inhibitors (for example, glyphosate), glutamine synthetase (GS) inhibitors (for example, glufosinate and phosphinothricin), synthetic auxins (for example, 2,4-D and dicamba). Examples of transgenes or transcribable polynucleotide molecules for use in practicing the invention include but are not limited to genes encoding proteins conferring tolerance to HPPD inhibitors (such as herbicide-insensitive HPPD), genes encoding proteins conferring tolerance to glufosinate (such as pat and bar), genes encoding proteins conferring tolerance to glyphosate (such as a glyphosate-tolerant EPSPS, such as cp4-epsps, provided herein as SEQ ID NO: 93), and genes encoding proteins conferring tolerance to a synthetic auxin such as dicamba (such as dicamba monooxygenase (DMO)) and 2,4-D (such as (R)-dichlorprop dioxygenase gene (rdpA)).

Recombinant DNA constructs of the invention may include the recombinant DNA molecules of the invention and are made by techniques known in the art and in various embodiments are included in plant transformation vectors, plasmids, or plastid DNA. Such recombinant DNA constructs are useful for producing transgenic plants and/or cells and as such can also be contained in the genomic DNA of a transgenic plant, seed, cell, or plant part. This invention therefore includes embodiments wherein the recombinant DNA construct is located within a plant transformation vector, or on a biolistic particle for transforming a plant cell, or within a chromosome or plastid of a transgenic plant cell, or within a transgenic cell, transgenic plant tissue, transgenic plant seed, transgenic pollen grain, or a transgenic or partially transgenic (for example, a grafted) plant. A vector is any DNA molecule that may be used for the purpose of plant transformation, i.e., the introduction of DNA into a cell. Recombinant DNA constructs of the invention can, for example, be inserted into a plant transformation vector and used for plant transformation to produce transgenic plants, seeds, and cells. Methods for constructing plant transformation vectors are well known in the art. Plant transformation vectors of the invention generally include, but are not limited to: a suitable promoter for the expression of an operably linked DNA, an operably linked recombinant DNA construct, and a polyadenylation signal (which may be included in a 3'UTR sequence). Promoters useful in practicing the invention include those that function in a plant for expression of an operably linked polynucleotide. Such promoters are varied and well known in the art and include those that are inducible, viral, synthetic, constitutive, temporally regulated, spatially regulated, and/or spatio-temporally regulated. Additional optional components include, but are not limited to, one or more of the following targets: 5' UTR, enhancer, cis-acting target, intron, signal sequence, transit peptide sequence, and one or more selectable marker genes. In one embodiment, a plant transformation vector comprises a recombinant DNA construct.

The recombinant DNA constructs and plant transformation vectors of this invention are made by any method suitable to the intended application, taking into account, for example, the type of expression desired, the transgene or transcribable polynucleotide molecule desired, and convenience of use in the plant in which the recombinant DNA construct is to be expressed. General methods useful for manipulating DNA molecules for making and using recombinant DNA constructs and plant transformation vectors are well known in the art and described in detail in, for example, handbooks and laboratory manuals including Michael R. Green and Joseph Sambrook, "Molecular Cloning: A Laboratory Manual" (Fourth Edition) ISBN:978-1-936113-42-2, Cold Spring Harbor Laboratory Press, NY (2012).

The recombinant DNA molecules and constructs of the invention can be modified by methods known in the art, either completely or in part, for example, for increased convenience of DNA manipulation (such as restriction enzyme recognition sites or recombination-based cloning sites), or for including plant-preferred sequences (such as plant-codon usage or Kozak consensus sequences), or to include sequences useful for recombinant DNA molecule and construct design (such as spacer or linker sequences). In certain embodiments, the DNA sequence of the recombinant DNA molecule and construct includes a DNA sequence that has been codon-optimized for the plant in which the recombinant DNA molecule or construct is to be expressed. For example, a recombinant DNA molecule or construct to be expressed in a plant can have all or parts of its sequence codon-optimized for expression in a plant by methods known in the art. The recombinant DNA molecules or constructs of the invention can be stacked with other recombinant DNA molecules or transgenic events for imparting additional traits (for example, in the case of transformed plants, traits including herbicide resistance, pest resistance, cold germination tolerance, water deficit tolerance) for example, by expressing or regulating other genes.

An aspect of the invention includes transgenic plant cells, transgenic plant tissues, and transgenic plants or seeds that include a recombinant DNA molecule of the invention. A further aspect of the invention includes artificial or recombinant plant chromosomes that include a recombinant DNA molecule of the invention. Suitable methods for transformation of host plant cells for use with the current invention include virtually any method by which DNA can be introduced into a cell (for example, where a recombinant DNA molecule is stably integrated into a plant chromosome) and are well known in the art. An exemplary and widely utilized method for introducing a recombinant DNA molecule into plants is the *Agrobacterium* transformation system, which is well known to those of skill in the art. Another exemplary method for introducing a recombinant DNA molecule into plants is insertion of a recombinant DNA molecule into a plant genome at a pre-determined site by methods of site-directed integration. Site-directed integration may be accomplished by any method known in the art, for example, by use of zinc-finger nucleases, engineered or native meganucleases, TALE-endonucleases, or an RNA-guided endonuclease (for example a CRISPR/Cas9 system). Transgenic plants can be regenerated from a transformed plant cell by the methods of plant cell culture. A transgenic plant homozygous with respect to a transgene can be obtained by sexually mating (selfing) an independent segregant transgenic plant that contains a single exogenous gene sequence to itself, for example a R0 or F0 plant, to produce R1 or F1 seed. One fourth of the R1 or F1 seed produced will be homozygous with respect to the transgene. Plants grown from germinating R1 or F1 seed can be tested for heterozygosity, typically using a SNP assay or a thermal amplification assay that allows for the distinction between heterozygotes and homozygotes (i.e., a zygosity assay).

The invention provides a transgenic plant having in its genome a recombinant DNA molecule of the invention, including, without limitation, alfalfa, cotton, maize, canola, rice, soybean, and wheat, among others. The invention also provides transgenic plant cells, plant parts, and progeny of such a transgenic plant. As used herein "progeny" includes any plant, seed, plant cell, and/or plant part produced from or regenerated from a plant, seed, plant cell, and/or plant part that included a recombinant DNA molecule of the invention. Transgenic plants, cells, parts, progeny plants, and seeds produced from such plants can be homozygous or heterozygous for the recombinant DNA molecule of the invention. Plant parts of the present invention may include, but are not limited to, leaves, stems, roots, seeds, endosperm, ovule, and pollen. Plant parts of the invention may be viable, nonviable, regenerable, or non-regenerable. The invention also includes and provides transformed plant cells comprising a DNA molecule of the invention. The transformed or transgenic plant cells of the invention include regenerable and non-regenerable plant cells.

Further included in this invention are embodiments wherein the recombinant DNA molecule is in a commodity product produced from a transgenic plant, seed, or plant part of this invention; such commodity products include, but are not limited to harvested parts of a plant, crushed or whole grains or seeds of a plant, or any food or non-food product comprising the recombinant DNA molecule of this invention.

The invention provides a method of inducing male-sterility in a transgenic plant comprising (a) growing a transgenic plant comprising a recombinant DNA molecule that comprises a heterologous transcribable polynucleotide molecule conferring herbicide tolerance operably linked to a mts-siRNA target element and (b) applying an effective amount of the herbicide to the transgenic plant to induce male-sterility. An effective amount of an herbicide is an amount sufficient to render a transgenic plant comprising a recombinant DNA molecule of the invention male-sterile. In one embodiment, an effective amount of glyphosate is about 0.125 pounds acid equivalent per acre to about 8 pounds acid equivalent per acre. The herbicide application may be applied prior to or during the development of the male reproductive tissue, such as at a stage selected from the group consisting of the V4, V5, V6, V7, V8, V9, V10, V11, V12, V13, and V14 stage of maize plant development and may prevent at least pollen development, pollen shed, or anther extrusion.

In one embodiment, the prevention of pollen development, pollen shed, or anther extrusion may result from male sterility and thus the absence of pollen development, pollen shed or anther extrusion may be an indication of male sterility. However, in some instances, male sterile plants may still develop small amounts of pollen. Therefore, in certain embodiments, the presence of a small amount of pollen does not necessarily indicate male fertile plants or a lack of male sterility.

Plant development is often determined by a scale of stages based on plant development. For maize, a common plant development scale used in the art is known as V-Stages. The V-stages are defined according to the uppermost leaf in which the leaf collar is visible. VE corresponds to emergence, V1 corresponds to first leaf, V2 corresponds to second leaf, V3 corresponds to third leaf, V(n) corresponds to nth leaf. VT occurs when the last branch of tassel is visible but before silks emerge. When staging a field of maize, each specific V-stage is defined only when 50 percent or more of the plants in the field are in or beyond that stage. Other development scales are known to those of skill in the art and may be used with the methods of the invention.

Another common tool for predicting and estimating stages of maize growth and development is Growing Degree Units (GDU). A factor in the growth and development of maize is heat. Heat is typically measured at a single point in time and is expressed as temperature, but it can also be measured over a period of time and be expressed as heat units. These heat units are commonly referred to as GDU's. GDU's may be defined as the difference between the average daily temperature and a selected base temperature subject to certain restrictions. GDU's are calculated using the following equation: Growing Degree Unit=$\{(H+L)/2\}-B$ where H is the daily high (but no higher than 86° F.), L is the daily low (but no lower than 50° F.), and B is the base of 50° F. Because maize growth is minor when temperatures are greater than 86° F. or less than 50° F., limits are set on the daily high and low temperatures used in the formula. The lower cutoff for daily temperature also prevents calculation of negative values. Therefore, if the daily high temperature exceeds 86° F., the daily high temperature used in the GDU formula would be set at 86° F. Conversely, if the daily low temperature drops below 50° F., the daily low temperature used in the GDU formula would be set at 50° F. If the daily high temperature does not exceed 50° F., then no GDU is recorded for that day. The maximum GDU a maize plant can accumulate in a day is 36, the minimum is zero. A maize plant's maturity rating is identified by the sum of the daily GDU values over a specified amount of time. The time period that most maize seed producers use is from the point of planting to physiological maturity or the point at which grain fill is virtually complete. In most U.S. states, for example, accumulated GDU's are kept for most geographic areas and are available from the USDA Crop Reporting Service or the State Extension Services. Additionally, an instrument for obtaining GDU information at a particular location is also described in U.S. Pat. No. 6,967,656, which is hereby incorporated by reference in its entirety herein.

Another method for predicting tassel development for determination of timing of male sterility inducing herbicide application is described in U.S. Pat. No. 8,618,358, which is hereby incorporated by reference in its entirety herein.

Herbicides for use with the invention include any herbicide including those active against acetyl coenzyme A carboxylase (ACCase), acetolactate synthase (ALS) inhibitors, photosystem II (PSII) inhibitors, protoporphyrinogen oxidase (PPO) inhibitors, 4-hydroxyphenyl pyruvate dioxygenase (HPPD) inhibitors, 5-enolypyruvyl shikimate 3-phosphate synthase (EPSPS) inhibitors, glutamine synthetase (GS) inhibitors, and synthetic auxins. Herbicides are well known in the art and described in, for example, "Modern Crop Protection Compounds, Volumes 1 (Second Edition), edited by Wolfgang Kramer, Ulrich Schirmer, Peter Jeschke, Matthias Witschel, ISBN: 9783527329656, Wiley-VCH Verlag GmbH & Co. KGaA, Germany (2012). In one embodiment, the herbicide is glyphosate.

Hybrid seed may be produced by using a method comprising (a) applying herbicide to a transgenic plant including a recombinant DNA molecule including a heterologous transcribable polynucleotide molecule conferring herbicide tolerance operably linked to a mts-siRNA target element, wherein the herbicide application is carried out during the development of the male reproductive tissue of the transgenic plant thereby inducing male-sterility in the transgenic plant; (b) fertilizing the transgenic plant with pollen from a second plant; and (c) harvesting hybrid seed from the transgenic plant. In one embodiment, the transgenic plant is maize. In one embodiment, the herbicide is glyphosate and the protein encoded by the heterologous transcribable polynucleotide molecule is a glyphosate-tolerant EPSPS. In one embodiment, the glyphosate is applied during the development at an effective amount of about 0.125 pounds acid equivalent per acre to about 8 pounds acid equivalent per acre. In another embodiment, the step of fertilizing may be accomplished by allowing natural fertilization, for instance through wind pollination, or may include mechanical or hand pollination.

Hybrid seed may be harvested from an male-sterile transgenic plant that has been fertilized with pollen from a second plant, wherein the male-sterile transgenic plant comprises a recombinant DNA molecule including a heterologous transcribable polynucleotide that confers herbicide tolerance operably linked to a mts-siRNA target element, and wherein the transgenic plant has been induced to be male-sterile by application of an effective amount of herbicide during the development of the male reproductive tissue. In one example, the herbicide is glyphosate and it is applied during the development at an effective amount of about 0.125 pounds acid equivalent per acre to about 8 pounds acid equivalent per acre and prevents at least pollen development, pollen shed, or anther extrusion.

EXAMPLES

The following examples describe improvements on hybrid seed production over those provided in the art. Such improvements include novel mts-siRNA targets and mts-siRNA target elements for use in recombinant DNA molecules and transgenic plants for providing early-stage pollen development arrest, resulting in the absence of viable pollen grains across a wide range of germplasm, and related methods of use. The following examples are provided to demonstrate embodiments of the invention.

Example 1: Identification of mts-siRNA Targets

Small RNA was isolated from four separate growth stages of maize tassel and three separate growth stages of maize ear. See Table 1. The tassel-enriched small RNA was isolated at very early tassel developmental stages (V7, V8/V9, V10/V11, and V12) (see FIG. 1). This produced small RNA from male tissues younger than that previously used in the art for obtaining tassel-enriched small RNA sequences.

Small RNA libraries were prepared using the isolated small RNA, and high-throughput small RNA sequencing was performed on the libraries. Bioinformatic analysis was used to compare the sequences in these tassel and ear libraries with the sequences in small RNA libraries prepared from other maize tissues including leaf collected at various growth stages, whole seedling, root collected at various growth stages, endosperm, and kernel. This differential bioinformatic analysis identified thousands of tassel-enriched small RNA sequences with normalized expression ranging from 10 to 665 transcripts per quarter million (tpq). The identified tassel-enriched small RNA sequences are likely siRNA because of their length (18-26 nucleotides) and their expected origin from a dsRNA precursor. Due to the male tissue specificity, these tassel-enriched small RNA are referred to herein as male tissue-specific-siRNA (mts-siRNA).

TABLE 1

Description of tassel and ear small RNA libraries

| Tassel/ear stage | Tassel/ear size |
|---|---|
| Tassel at Microspore mother cell stage (plant at V7-V8) | <1 cm |
| Tassel at Microspore mother cell stage-premeiosis (plant at V8-V9) | 1-3 cm |
| Tassel at early meiosis - free microspore stage (plant at V9-V10) | 3-17 cm |
| Tassel at later stage - uninucleate microspores (plant at V12-VT) | >17 cm |
| Ear at premieosis - four-nucleate immature embryo sac stage (plant at VT) | 2-3 cm |
| Ear at 8-nucleate immature embryo sac stage to later stage with up to 10 antipodal cells (plant at VT) | 4-5 cm |
| Ear at the stage of pollination (plant at VT-R1) | 9-10 cm |

A real-time PCR method was used for identification and confirmation that the mts-siRNA sequences were specifically expressed in tassel. Total RNA, including enriched small RNA, was extracted from the tissues indicated in Table 1 and used to synthesize cDNA with reverse transcription primers consisting of 8 nt complementary to the mts-siRNA sequences on the 3' end and a 35 nt universal sequence on the 5' end. Following cDNA synthesis, real-time PCR was performed where the sequence (14 to 18 nt) of one of the forward primers was identical to the 5'-end of a mts-siRNA sequence and the reverse primer was a universal primer. As an internal control, 18S RNA was amplified and this was used to normalize the mts-siRNA levels. The data from the real-time PCR was used to narrow the number of mts-siRNA sequences that were enriched in tassel.

A siRNA profiling microarray assay was performed using μParaflo® Microfluidics chips provided by LC Sciences LLC (Houston, Tex., USA) with 1,200 sequences selected from the thousands of mts-siRNA sequences identified from the differential bioinformatic analysis. The microarray chips contained triplicate probes of the complementary sequence for each of the 1,200 mts-siRNA sequences. Total RNA was purified from 26 maize tissue pools (duplicate or triplicate tissue pools) from either LH244 (ATCC deposit number PTA-1173) or 01DKD2 (I294213) (ATCC deposit number PTA-7859) inbred plants. See Table 2. Each of the 26 RNA samples were hybridized with the microarray chips that contain probes for the 1,200 mts-siRNA. Hybridization images were collected using a GenePix® 4000B laser scanner (Molecular Devices, Sunnyvale, Calif.) and digitized using Array-Pro® Analyzer image analysis software (Media Cybernetics, Rockville, Md.). Relative signal values were derived by background subtraction and normalization. Differentially expressed signals were determined by t-test with $p<0.05$. From the microarray analysis, about 500 mts-siRNA from the 1,200 were identified as being highly tassel-specific.

TABLE 2

Description of tissue samples used in microarray assay.

| Chip Number | Genotype | Tissue type | Samples pooled from 3 plants | Stage |
|---|---|---|---|---|
| 1 | LH244 | Younger ear | <5 cm pooled | VT |
| 2 | LH244 | Older ear | >5 cm pooled | VT-R1 |
| 3 | LH244 | Younger tassel | 2-7 cm pooled | V8-V9 |
| 4 | LH244 | Older tassel | >7 cm pooled | V10-V12 |
| 5 | LH244 | leaf | V4 pooled | V4 |
| 6 | LH244 | leaf | V12 pooled | V12 |
| 7 | LH244 | root | V4 pooled | V4 |
| 8 | LH244 | stem | V4 pooled | V4 |
| 9 | LH244 | Younger ear | <5 cm pooled | VT |
| 10 | LH244 | Older ear | >5 cm pooled | VT-R1 |
| 11 | LH244 | Younger tassel | 2-7 cm pooled | V8-V9 |
| 12 | LH244 | Older tassel | >7 cm pooled | V10-V12 |
| 13 | LH244 | leaf | V4 pooled | V4 |
| 14 | LH244 | leaf | V12 pooled | V12 |
| 15 | LH244 | root | V4 pooled | V4 |
| 16 | LH244 | root | V4 pooled | V4 |
| 17 | 01DKD2 | Younger ear | <5 cm pooled | VT |
| 18 | 01DKD2 | Older ear | >5 cm pooled | VT-R1 |
| 19 | 01DKD2 | Older ear | >5 cm pooled | VT-R1 |
| 20 | 01DKD2 | Younger tassel | 2-7 cm pooled | V8-V9 |
| 21 | 01DKD2 | Younger tassel | 2-7 cm pooled | V8-V9 |
| 22 | 01DKD2 | Older tassel | >7 cm pooled | V10-V12 |
| 23 | 01DKD2 | Older tassel | >7 cm pooled | V10-V12 |
| 24 | 01DKD2 | Leaf | V4 pooled | V4 |
| 25 | LH244 | leaf | V4 pooled | V4 |
| 26 | LH244 | leaf | V12 pooled | V12 |

Figure 2:
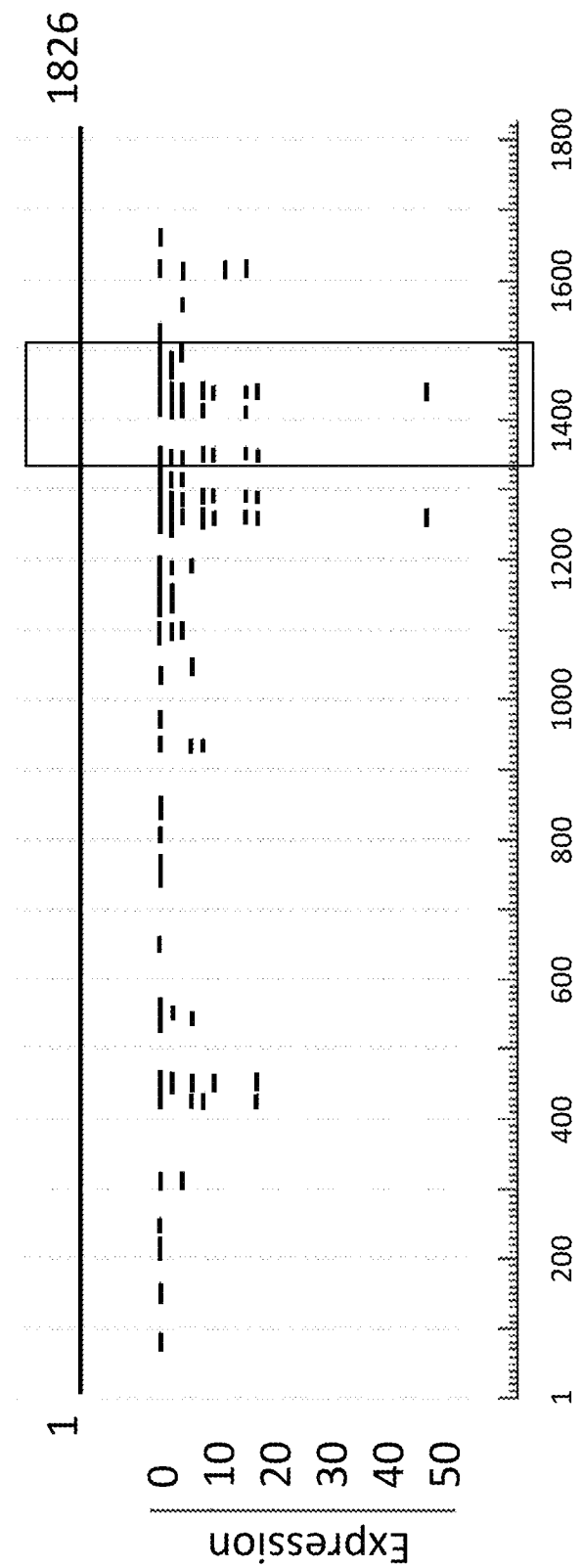
FIG. 2. Graphical representation of alignment of mts-siRNA sequences on the cDNA sequence provided as SEQ ID NO: 17. The cDNA sequence is indicated from nucleotide 1 to 1826, and the short lines represent the alignment of the complementary strand of individual mts-siRNA sequences, or stretches of adjacent mts-siRNA sequences or overlapping mts-siRNA sequences (relatively longer lines) to the cDNA sequence. The mts-siRNA sequences which are the same strand as the cDNA are not shown. The normalized relative expression level of mts-siRNA is indicated on the left. The boxed area represents a region of the cDNA sequence rich in mts-siRNA targets.

Bioinformatic analysis was then done using sequence alignment tools such as Basic Local Alignment Search Tool (BLAST) or SHort Read Mapping Package (SHRiMP) (Rumble, 2009) to compare the 500 mts-siRNA sequences identified as being highly tassel-specific against a unigene collection of maize cDNA sequences. This BLAST analysis revealed maize cDNA sequences to which many mts-siRNA sequences aligned resulting in identifiable DNA sequence regions having clustered, overlapping alignments of multiple mts-siRNA sequences with perfect or near perfect matches. Six cDNA sequences were identified from this analysis as containing one or more such regions rich in mts-siRNA target sequences. These six cDNA sequences are provided herein as SEQ ID NO: 17; SEQ ID NO: 18; SEQ ID NO: 19; SEQ ID NO: 20; SEQ ID NO: 21; and SEQ ID NO: 22. As an example, FIG. 2 shows a graphical representation of the alignment of multiple mts-siRNA sequences on the cDNA provided as SEQ ID NO: 17. The multiple short lines represent the relative position of mts-siRNA target sequences (and therefore the location of the binding site for the mts-siRNA in the transcribed mRNA molecule) that align to the cDNA. The Y-axis represents normalized expression levels of mts-siRNA in male tissues as detected in the microarray analysis. The box represents the region of the cDNA SEQ ID NO: 17 corresponding to the mts-siRNA target element sequences SEQ ID NO: 1 and SEQ ID NO: 2.

Selected mts-siRNA sequences aligning to one of the six cDNA sequences were used for further microarray analysis to determine differential expression across maize tissues. Microarray analysis for mts-siRNA sequences of normalized signal values for V8-V9 tassel, V10-V12 tassel, or combined signals from the other tissue for maize germplasm LH244 and 01DKD2 is presented in Tables 3-10. Each table shows a subset of mts-siRNA sequences identified as aligning to one of six cDNA sequences provided herein as SEQ ID NO: 17; SEQ ID NO: 18; SEQ ID NO: 19; SEQ ID NO: 20; SEQ ID NO: 21; and SEQ ID NO: 22. Signal value results are measured as relative signal values and standard error ($p<0.05$) is represented by (STDR). The microarray results illustrate that the representative mts-siRNA sequences give a high signal in tassel (V8-V9 and V10-V12) and a low signal in other tissue which indicates that endogenous expression of these mts-siRNA is highly enriched in tassel. The mts-siRNA sequence corresponds to the sense or antisense strand of the corresponding mts-siRNA target sequence in the cDNA sequence. The mts-siRNA sequence may have a single nucleotide, a two nucleotide, or a three nucleotide mismatch with the aligned portion of the cDNA sequence, and the mts-siRNA sequence may align to the sense strand or antisense strand of the cDNA sequence. The mts-siRNA sequences provided here are found across different maize germplasms.

Table 3 shows relative microarray signal results for representative mts-siRNA sequences (provided herein as SEQ ID NO: 23-31) that align to the cDNA sequence provided herein as SEQ ID NO: 17, which contains the mts-siRNA target element sequences represented by SEQ ID NO: 1 and SEQ ID NO: 2. For both germplasm LH244 and 01DKD2, the signals for these mts-siRNA sequences in V8-V9 tassel and V10-V12 tassel are higher than the signal for these mts-siRNA sequences for the other tissue samples. The microarray results shown in Table 3 indicate that the cDNA sequence provided herein as SEQ ID NO: 17 can be used as a source to design mts-siRNA target elements for recombinant DNA molecules.

TABLE 3

Microarray results for cDNA of SEQ ID NO: 17

| | LH244 | | | 01DKD2 | | |
|---|---|---|---|---|---|---|
| SEQ ID NO: | V8-V9 Tassel (STDR) | V10-V12 Tassel (STDR) | Other Tissue (STDR) | V8-V9 Tassel (STDR) | V10-V12 Tassel (STDR) | Other Tissue (STDR) |
| 23 | 183.5 (36.9) | 514 (105.2) | 2.6 (0.6) | 27 (2) | 318 (46.5) | 4.3 (1.5) |
| 24 | 104.5 (40.9) | 322 (77.5) | 7.7 (3.5) | 16 (1) | 174 (32.3) | 3 (0.7) |
| 25 | 289 (99) | 824.3 (146.6) | 2.6 (0.7) | 56 (9.1) | 440 (14.1) | 2.3 (1.1) |
| 26 | 55.5 (4.5) | 175.7 (41.2) | 3.8 (1.1) | 10 (7.1) | 104 (26.3) | 3.8 (1.8) |
| 27 | 377.5 (60.1) | 581.7 (76.8) | 1.1 (0.3) | 73 (10.1) | 405.5 (3.5) | 1 (0.4) |
| 28 | 126.5 (32.8) | 248 (46.1) | 2.4 (1.4) | 29 (11.1) | 134.5 (31.8) | 3.8 (1) |
| 29 | 292.5 (25.8) | 886.7 (99.7) | 2.2 (0.7) | 86 (11.1) | 535.5 (20.7) | 4 (1.2) |
| 30 | 173.5 (52) | 495.7 (80.9) | 4.2 (1.1) | 32 (1) | 282 (20.2) | 6.5 (1.9) |
| 31 | 8 (3) | 49 (15.8) | 1.2 (0.4) | 0 (0) | 26.5 (6.6) | 2.8 (0.6) |

Table 4 shows relative microarray signal results for representative mts-siRNA sequences (provided herein as SEQ ID NO: 32-38) that align to the cDNA sequence provided herein as SEQ ID NO: 18, which contains the mts-siRNA target element sequence represented by SEQ ID NO: 3. For germplasm LH244, the signals for these mts-siRNA sequences in V8-V9 tassel and V10-V12 tassel are higher than the signals for these mts-siRNA sequences for the other tissue samples. For germplasm 01DKD2, the signals for these mts-siRNA sequences are higher in V10-V12 tassel than the signals for these mts-siRNA sequences for the V8-V9 tassel or the other tissue samples.

TABLE 4

Microarray results for cDNA of SEQ ID NO: 18

| | LH244 | | | 01DKD2 | | |
|---|---|---|---|---|---|---|
| SEQ ID NO: | V8-V9 Tassel (STDR) | V10-V12 Tassel (STDR) | Other Tissue (STDR) | V8-V9 Tassel (STDR) | V10-V12 Tassel (STDR) | Other Tissue (STDR) |
| 32 | 376.5 (320.7) | 118 (30.8) | 2 (0.6) | 7.5 (3.5) | 516 (307.1) | 2.8 (0.9) |
| 33 | 111.5 (12.6) | 1032.7 (26.8) | 17.8 (13.1) | 4.5 (2.5) | 648.5 (174.3) | 2.8 (1) |
| 34 | 848.5 (675.3) | 572.7 (211.3) | 3 (0.6) | 8.5 (0.5) | 982 (389.9) | 3.5 (1.3) |
| 35 | 437 (370.7) | 117.7 (22.8) | 1.6 (0.6) | 4 (3) | 519 (319.2) | 2.8 (0.5) |
| 36 | 906.5 (668.2) | 606.7 (231.5) | 2.2 (0.7) | 15.5 (1.5) | 1225.5 (480.3) | 4.3 (1.5) |
| 37 | 554 (370.7) | 553 (48.5) | 1.5 (0.4) | 9.5 (1.5) | 1224.5 (153) | 3.3 (1.4) |
| 38 | 768.5 (480.3) | 1442.7 (17.2) | 1.4 (0.5) | 8.5 (2.5) | 1305.5 (10.6) | 3 (1.5) |

Table 5 shows relative microarray signal results for representative mts-siRNA sequences (provided herein as SEQ ID NO: 39-42) that align to the cDNA sequence provided herein as SEQ ID NO: 18, which contains the mts-siRNA target element sequence represented by SEQ ID NO: 4. For germplasm LH244, the signals for the mts-siRNA sequences in V8-V9 tassel and V10-V12 tassel are higher than the signal for these mts-siRNA sequences for the other tissue samples. For germplasm 01DKD2, the signals for the mts-siRNA sequences are higher in V10-V12 tassel than the signal for these mts-siRNA sequences for the V8-V9 tassel or the other tissue samples. The microarray results shown in Table 4 and Table 5 indicate that the cDNA sequence provided herein as SEQ ID NO: 18 can be used as a source to design mts-siRNA target elements for recombinant DNA molecules.

TABLE 5

Microarray results for cDNA of SEQ ID NO: 18

| | LH244 | | | 01DKD2 | | |
|---|---|---|---|---|---|---|
| SEQ ID NO: | V8-V9 Tassel (STDR) | V10-V12 Tassel (STDR) | Other Tissue (STDR) | V8-V9 Tassel (STDR) | V10-V12 Tassel (STDR) | Other Tissue (STDR) |
| 39 | 442.5 (242.9) | 2157.3 (1059.3) | 0.6 (0.2) | 16 (12.1) | 1514.5 (525.8) | 1.5 (1.5) |
| 40 | 119 (2) | 448.7 (125.1) | 1.5 (0.5) | 7.5 (0.5) | 452 (97) | 2.8 (0.9) |
| 41 | 185.5 (19.7) | 702.7 (195.2) | 0.9 (0.3) | 5 (1) | 752 (225.3) | 3 (1.5) |
| 42 | 143.5 (7.6) | 564.3 (154.3) | 2.6 (0.8) | 6 (1) | 588 (163.6) | 5.3 (1.5) |

Table 6 shows relative microarray signal results for representative mts-siRNA sequences (provided herein as SEQ ID NO: 43-46) that align to the cDNA sequence provided herein as SEQ ID NO: 19, which contains the mts-siRNA target element sequence represented by SEQ ID NO: 5. For germplasm LH244, the signals for the mts-siRNA sequences in V8-V9 tassel and V10-V12 tassel are higher than the signal for these mts-siRNA sequences for the other tissue samples. For germplasm 01DKD2, the signal for the mts-siRNA sequences (SEQ ID NO: 43-44) is higher in V10-V12 tassel than the signal for these mts-siRNA sequences for the V8-V9 tassel or the other tissue samples; and the signals for the mts-siRNA sequences (SEQ ID NO: 45-46) are higher than the signal for these mts-siRNA sequences in both V8-V9 tassel and V10-V12 tassel compared to the other tissue sample.

TABLE 6

Microarray results for cDNA of SEQ ID NO: 19

| | LH244 | | | 01DKD2 | | |
|---|---|---|---|---|---|---|
| SEQ ID NO: | V8-V9 Tassel (STDR) | V10-V12 Tassel (STDR) | Other Tissue (STDR) | V8-V9 Tassel (STDR) | V10-V12 Tassel (STDR) | Other Tissue (STDR) |
| 43 | 52.5 (29.8) | 147.3 (13.2) | 1 (0.3) | 4 (0) | 190.5 (2.5) | 4.3 (2.4) |
| 44 | 756 (548.5) | 1340 (75) | 1.8 (0.5) | 15.5 (1.5) | 1443.5 (85.4) | 6.3 (1.7) |
| 45 | 7901 (1803.1) | 9982.3 (2999) | 8.2 (5.4) | 253 (11.1) | 7195.5 (759.1) | 5.8 (4.1) |
| 46 | 4502.5 (424.8) | 8663.3 (1595.4) | 8.4 (6.2) | 252 (9.1) | 6778 (124.2) | 6.8 (3.8) |

Table 7 shows relative microarray signal results for representative mts-siRNA sequences (provided herein as SEQ ID NO: 47-52) that align to the cDNA sequence provided herein as SEQ ID NO: 19, which contains the mts-siRNA target element sequence represented by SEQ ID NO: 6. For germplasm LH244, the signals for the mts-siRNA sequences in V8-V9 tassel and V10-V12 tassel are higher than the signal for these mts-siRNA sequences for the other tissue samples. For germplasm 01DKD2, the signals for the mts-siRNA sequences are higher in V10-V12 tassel than the signal for these mts-siRNA sequences in the V8-V9 tassel or the other tissue samples; the signals for the mts-siRNA sequences (SEQ ID NO: 47 and SEQ ID NO: 48) are moderately higher in V8-V9 tassel compared to the signal for these mts-siRNA sequences for the other tissue sample; the signal for the mts-siRNA sequence (SEQ ID NO: 52) is significantly higher in V8-V9 tassel compared to the signal for this mts-siRNA sequence for the other tissue sample; and the signals for mts-siRNA sequences (SEQ ID NO: 49, SEQ ID NO: 50, and SEQ ID NO: 51) are not significantly different from the signal for these mts-siRNA sequences for the other tissue samples. The microarray results shown in Table 6 and Table 7 indicate that the cDNA sequence provided herein as SEQ ID NO: 19 can be used as a source to design mts-siRNA target elements for recombinant DNA molecules.

TABLE 7

Microarray results for cDNA of SEQ ID NO: 19

| | LH244 | | | 01DKD2 | | |
|---|---|---|---|---|---|---|
| SEQ ID NO: | V8-V9 Tassel (STDR) | V10-V12 Tassel (STDR) | Other Tissue (STDR) | V8-V9 Tassel (STDR) | V10-V12 Tassel (STDR) | Other Tissue (STDR) |
| 47 | 157.5 (5.6) | 900.7 (51.8) | 15.5 (7.4) | 12.5 (1.5) | 1051.5 (199.5) | 4 (0.7) |
| 48 | 221 (106.1) | 720.3 (251.7) | 4.8 (2.7) | 9.5 (6.6) | 470.5 (57.1) | 1 (0.4) |
| 49 | 340 (239.4) | 1241.7 (105.7) | 16.3 (5.4) | 57.5 (10.6) | 867 (117.2) | 55.3 (11.6) |
| 50 | 296 (228.3) | 722 (267.2) | 0 (0) | 5.5 (5.6) | 326 (262.6) | 1.8 (1.8) |
| 51 | 158 (78.8) | 287 (46) | 34.3 (6.5) | 24.5 (0.5) | 275.5 (20.7) | 40 (3.1) |
| 52 | 4080 (1829.4) | 3629.7 (1327.5) | 5.5 (3.5) | 234 (11.1) | 3286.5 (33.8) | 3.5 (2.1) |

Table 8 shows relative microarray signal results for representative mts-siRNA sequences (provided herein as SEQ ID NO: 53-60) that align to the cDNA sequence provided herein as SEQ ID NO: 20, which contains the mts-siRNA target element sequence represented by SEQ ID NO: 7. For both germplasm LH244 and 01DKD2, the signals for these mts-siRNA sequences in V8-V9 tassel and V10-V12 tassel are higher than the signal for these mts-siRNA sequences for the other tissue samples. The microarray results shown in Table 8 indicate that the cDNA sequence provided herein as SEQ ID NO: 20 can be used as a source to design mts-siRNA target elements for recombinant DNA molecules.

TABLE 8

Microarray results for cDNA of SEQ ID NO: 20

| SEQ ID NO: | LH244 | | | 01DKD2 | | |
|---|---|---|---|---|---|---|
| | V8-V9 Tassel (STDR) | V10-V12 Tassel (STDR) | Other Tissue (STDR) | V8-V9 Tassel (STDR) | V10-V12 Tassel (STDR) | Other Tissue (STDR) |
| 53 | 76.5 (1.5) | 145 (19.4) | 2.2 (0.8) | 16 (2) | 84 (1) | 1.5 (0.5) |
| 54 | 100.5 (3.5) | 172 (21.6) | 14.2 (6.2) | 56 (22.2) | 231 (79.8) | 19.5 (4.7) |
| 55 | 377.5 (60.1) | 581.7 (76.8) | 1.1 (0.3) | 73 (10.1) | 405.5 (3.5) | 1 (0.4) |
| 56 | 261 (1) | 692 (59.7) | 49.5 (30.4) | 138.5 (29.8) | 599.5 (41.9) | 19.3 (4.8) |
| 57 | 126.5 (32.8) | 248 (46.1) | 2.4 (1.4) | 29 (11.1) | 134.5 (31.8) | 3.8 (1) |
| 58 | 215.5 (14.6) | 349 (29.1) | 0.7 (0.3) | 88.5 (2.5) | 327 (31.3) | 2 (0.9) |
| 59 | 789 (97) | 1262.7 (169.2) | 4.1 (2.6) | 202 (24.2) | 811.5 (115.7) | 0.3 (0.3) |
| 60 | 141.5 (9.6) | 265.7 (30.1) | 5.8 (1.2) | 75.5 (5.6) | 303 (37.4) | 9.3 (1.8) |

Table 9 shows relative microarray signal results for representative mts-siRNA sequences (provided herein as SEQ ID NO: 61-69) that align to the cDNA sequence provided herein as SEQ ID NO: 21, which contains the mts-siRNA target element sequence represented by SEQ ID NO: 8. For both germplasm LH244 and 01DKD2, the signals for the mts-siRNA sequences in V8-V9 Tassel and V10-V12 tassel is higher than the signal for these mts-siRNA sequences for the other tissue samples. The microarray results shown in Table 9 indicate that the cDNA sequence provided herein as SEQ ID NO: 21 can be used as a source to design mts-siRNA target elements for recombinant DNA molecules.

TABLE 9

Microarray results for cDNA of SEQ ID NO: 21

| SEQ ID NO: | LH244 | | | 01DKD2 | | |
|---|---|---|---|---|---|---|
| | V8-V9 Tassel (STDR) | V10-V12 Tassel (STDR) | Other Tissue (STDR) | V8-V9 Tassel (STDR) | V10-V12 Tassel (STDR) | Other Tissue (STDR) |
| 61 | 850.5 (8.6) | 334.7 (222.3) | 9.4 (3.4) | 461 (154.6) | 454 (1) | 8 (5) |
| 62 | 44.5 (5.6) | 11.3 (3.9) | 1.8 (0.7) | 13.5 (5.6) | 15.5 (6.6) | 1 (1) |
| 63 | 34.5 (4.5) | 11.7 (2.2) | 3.2 (1) | 14.5 (1.5) | 18 (1) | 1.5 (0.5) |
| 64 | 23 (8.1) | 13.7 (4.6) | 1.8 (1) | 13.5 (13.6) | 9 (8.1) | 1.3 (0.9) |
| 65 | 811.5 (169.2) | 260.3 (103.2) | 5.8 (2.7) | 444.5 (4.5) | 454.5 (45) | 12 (8.4) |
| 66 | 199.5 (54) | 48 (20.6) | 1.9 (0.7) | 61 (44.4) | 55.5 (34.9) | 2.8 (1.8) |
| 67 | 216 (18.2) | 62 (16.6) | 3.3 (2) | 123.5 (0.5) | 107 (17.2) | 4.3 (2.6) |
| 68 | 265 (86.9) | 85.3 (20.4) | 5 (2.3) | 98 (62.6) | 96 (56.6) | 2.5 (2.2) |
| 69 | 516 (82.8) | 185 (82.1) | 11.2 (4.1) | 309.5 (19.7) | 282.5 (2.5) | 9.8 (5.5) |

Table 10 shows relative microarray signal results for representative mts-siRNA sequences (provided herein as SEQ ID NO: 70-87) that align to the cDNA sequence provided herein as SEQ ID NO: 22, which contains the mts-siRNA target element sequence represented by SEQ ID NO: 9. For germplasm LH244, the signals for the mts-siRNA sequences (SEQ ID NO: 70, 71, 73, 75-81, 83-87) in V8-V9 tassel and V10-V12 tassel are higher than the signal for these mts-siRNA sequences for the other tissue samples; and the signals for the mts-siRNA sequences (SEQ ID NO: 72, 74, 82) in other tissue was higher than the signal for these mts-siRNA sequences in either the V8-V9 tassel or the V10-V12 tassel. For germplasm 01DKD2, the signals for the mts-siRNA sequences (SEQ ID NO: 70-87) are higher in V10-V12 tassel than the signal for these mts-siRNA sequences in the V8-V9 tassel or the other tissue samples. The microarray results shown in Table 10 indicate that the cDNA sequence provided herein as SEQ ID NO: 22 can be used as a source to design mts-siRNA target elements for recombinant DNA molecules.

plasms tested. The sequence of the amplicon across the thirty-two germplasms was either 100% identical to the mts-siRNA target element sequence or contained a minimal number of single nucleotide polymoprhisms (up to 95% identical). These data indicate that transgenic plants generated with a recombinant DNA construct comprising a transgene encoding a recombinant protein operably linked to a mts-siRNA target element provided as SEQ ID NO: 1 or SEQ ID NO: 2 would have male tissue specific regulation of the expression of the recombinant protein across most maize germplasms. If the transgene encodes a recombinant protein conferring glyphosate tolerance, then the tassels across most maize germplasm would have glyphosate-induced male sterility.

Example 2: Recombinant DNA Constructs and Plant Transformation Vectors

Recombinant DNA constructs and plant transformation vectors were created using DNA sequences corresponding to

TABLE 10

Microarray results for cDNA of SEQ ID NO: 22

| | LH244 | | | 01DKD2 | | |
|---|---|---|---|---|---|---|
| SEQ ID NO: | V8-V9 Tassel (STDR) | V10-V12 Tassel (STDR) | Other Tissue (STDR) | V8-V9 Tassel (STDR) | V10-V12 Tassel (STDR) | Other Tissue (STDR) |
| 70 | 56.5 (23.7) | 694 (256.9) | 1.8 (0.4) | 3 (3) | 873 (308.1) | 4 (1.5) |
| 71 | 1125.5 (383.4) | 2380 (696.9) | 1.6 (0.5) | 46 (0) | 1943.5 (447) | 2.3 (1.3) |
| 72 | 323.5 (54) | 325.7 (55.9) | 1324.8 (1083.3) | 332.5 (83.3) | 530 (89.9) | 233.3 (16.5) |
| 73 | 1058.5 (370.2) | 2395.7 (634.9) | 4.5 (1.8) | 37.5 (2.5) | 1695.5 (380.3) | 2 (1.4) |
| 74 | 83.5 (20.7) | 129 (11.2) | 164.2 (106.5) | 43.5 (0.5) | 171 (19.2) | 45.8 (4.5) |
| 75 | 53 (34.3) | 237.3 (62.1) | 3.3 (0.5) | 3 (1) | 257 (74.8) | 5 (1.8) |
| 76 | 55 (38.4) | 252.3 (66.5) | 5.7 (1) | 2.5 (0.5) | 276.5 (81.3) | 4 (1.4) |
| 77 | 180.5 (64.1) | 302.7 (111.2) | 4.1 (2.3) | 0.5 (0.5) | 225 (30.3) | 2.5 (0.6) |
| 78 | 47.5 (15.7) | 642.7 (242) | 1 (0.4) | 3 (2) | 715.5 (211.6) | 4.5 (1) |
| 79 | 197.5 (62.1) | 269.3 (106.8) | 1.9 (0.6) | 5 (1) | 290.5 (28.8) | 2 (0.4) |
| 80 | 138 (83.8) | 383.3 (44.6) | 0.7 (0.3) | 2.5 (1.5) | 230 (43.4) | 0.5 (0.3) |
| 81 | 207 (113.1 | 470.3 (55.2) | 1.6 (1.1) | 1 (1) | 320 (69.7) | 0 (0) |
| 82 | 95.5 (29.8) | 137 (17.7) | 217.4 (158.6) | 71.5 (7.6) | 211 (14.1) | 54.8 (5.1) |
| 83 | 173 (63.6) | 303 (82) | 2.5 (1.2) | 2 (1) | 253.5 (24.7) | 1.5 (0.6) |
| 84 | 13 (5.1) | 35.7 (7.1) | 4.4 (1.5) | 0 (0) | 20 (10.1) | 1 (0.4) |
| 85 | 184 (71.7) | 310 (109.1) | 2.8 (1.3) | 2.5 (0.5) | 246 (14.1) | 2.5 (1) |
| 86 | 173.5 (62.1) | 241.7 (101.2) | 2.4 (0.7) | 3 (1) | 256.5 (7.6) | 3 (0.9) |
| 87 | 56 (35.4) | 104 (12.7) | 4.7 (2) | 25 (0.5) | 91.5 (6.6) | 2.5 (1) |

These analyses confirmed that the six cDNA sequences (SEQ ID NO: 17-22) were rich in mts-siRNA target sequences and that the corresponding mts-siRNA showed high tassel specificity. These cDNA sequences thus contain sequences useful with the methods of molecular biology for creating recombinant DNA molecules that contain mts-siRNA target elements which may confer mts-siRNA mediated transgene silencing.

Analysis of the corresponding genomic sequence containing the mts-siRNA target elements was conducted for thirty-two different maize germplasms (with relative maturity (RM) ranging from 80 to 120 days) typically used as a female in a hybrid cross to confirm the presence and any sequence variation of the mts-siRNA target elements. For the mts-siRNA target elements provided as SEQ ID NO: 1 and SEQ ID NO: 2, three sets of thermal amplification primer pairs were designed to amplify the corresponding sequence within the cDNA sequence provided here as SEQ ID NO: 17. These primers were used to generate a PCR amplicon in genomic DNA extracted from tissue of each germplasm. Amplicons were produced from all of the germregions of the six cDNA sequences identified as rich in mts-siRNA target sequences. The recombinant DNA constructs and plant transformation vectors were designed to be useful for producing transgenic plants in which tassel-specific silencing of a transgene operably linked to a mts-siRNA target element would occur via mts-siRNA mediated silencing.

Nine mts-siRNA target elements were designed using the results of the analysis of the six cDNA sequences. Each mts-siRNA target element was designed to have a DNA sequence comprising many overlapping mts-siRNA target sequences to which different mts-siRNA may bind. The mts-siRNA target element sequence provided herein as SEQ ID NO: 1 has 95% sequence identity to nucleotide position 1429 to 1628 of the cDNA sequence provided herein as SEQ ID NO: 17. The mts-siRNA target element sequence provided herein as SEQ ID NO: 2 has a single nt change (T69A) relative to SEQ ID NO: 1. The mts-siRNA target element sequence provided herein as SEQ ID NO: 3 corresponds to nucleotide position 239 to 433 of the cDNA sequence provided herein as SEQ ID NO: 18. The mts-siRNA target element sequence provided herein as SEQ ID NO: 4 corresponds to nucleotide position 477 to 697 of the cDNA sequence provided herein as SEQ ID NO: 18. The mts-siRNA target element sequence provided herein as SEQ ID NO: 5 corresponds to nucleotide position 239 to 433 of the cDNA sequence provided herein as SEQ ID NO: 19. The mts-siRNA target element sequence provided herein as SEQ ID NO: 6 corresponds to nucleotide position 370 to 477 of the cDNA sequence provided herein as SEQ ID NO: 19. The mts-siRNA target element sequence provided herein as SEQ ID NO: 7 corresponds to nucleotide position 1357 to 1562 of the cDNA sequence provided herein as SEQ ID NO: 20. The mts-siRNA target element sequence provided herein as SEQ ID NO: 8 corresponds to nucleotide position 247 to 441 of the cDNA sequence provided herein as SEQ ID NO: 21. The reverse complement of the mts-siRNA target element sequence represented by SEQ ID NO: 9 has a 99% sequence identity to nucleotide position 191 to 490 of the cDNA sequence provided herein as SEQ ID NO: 22 with three nt mismatches (C314A, A350G, and G408A) of SEQ ID NO: 22 relative to the sequence of the reverse complement of SEQ ID NO: 9. Additional mts-siRNA target elements can be created by combining the DNA sequences of different mts-siRNA target elements or fragments of two or more mts-siRNA target rich cDNA regions, such as by combining all or fragments of two or more of the mts-siRNA target elements provided herein as SEQ ID NO: 1-9 and/or one or more of the mts-siRNA sequences provided herein as SEQ ID NO: 23-92. Different fragments of these mts-siRNA target elements ranging in length from 21 to 170 nucleotides were combined and new mts-siRNA target elements were produced using methods of DNA synthesis known in the art and are provided as SEQ ID NO: 10-16.

The mts-siRNA target elements were subcloned into recombinant DNA constructs with the mts-siRNA target element operably linked to the 3' end of the open reading frame of the cp4-epsps gene (SEQ ID NO: 93), encoding the CP4-EPSPS protein for glyphosate tolerance, and 5' to the operably linked 3'-untranslated region (3'-UTR). The recombinant DNA constructs also contained operably linked combinations of one of three different promoter/intron/enhancer combinations and a chloroplast transit peptide sequence. Expression cassette configurations contained in transformation vectors for testing mts-siRNA target effectiveness.

Example 3: Plant Transformation and Efficacy Testing

Transformation vectors containing the recombinant DNA constructs were used with an *Agrobacterium*-based transformation method and maize immature embryos and techniques known in the art. Leaf samples of R0 plants were collected and molecular analysis was conducted to select transgenic plants containing a single copy (one insertion) or a double copy (two independent insertions) of the recombinant DNA construct and no presence of vector backbone. Single copy events were not sprayed with glyphosate and were selfed and advanced for R1 seed collection, while double copy events were used for R0 glyphosate spray to assess vegetative tolerance and induced male sterility. Transgenic plants that were not sprayed with glyphosate had normal anthesis, normal pollen shedding, and normal pollen development as determined by Alexandar staining and microscopic observation.

Double copy R0 events were used in testing to approximate a single copy homozygous event. Plants were sprayed with glyphosate at two different growth stages to determine if the presence of the mts-siRNA target element in the recombinant DNA construct provided vegetative glyphosate tolerance and glyphosate-induced tassel sterility. The plants were sprayed in a greenhouse with 1× glyphosate (0.75 lb ae/acre) applied at the V5 stage followed by 1× glyphosate (0.75 lb ae/acre) applied at the V8 stage. Seven days after the V5 stage glyphosate application, plants were scored for vegetative injury with scores of ≤10% injury considered as showing vegetative glyphosate tolerance (% Vegetative Tolerant). Male sterility was measured in two ways. Plants that showed vegetative glyphosate tolerance were scored after the V8 stage glyphosate application for complete glyphosate-induced male sterility measured as no anther extrusion up to the S90+12 stage (% Completely Male-sterile). Anthers were then collected and dissected to microscopically observe pollen development. Anthers for each event were tested for no viable pollen grains produced as detected by Alexandar staining under microscopic observation and scored as not producing any viable pollen (% No Pollen). In plants not sprayed with glyphosate, tassel development, anther extrusion, and pollen development were normal.

The mts-siRNA target elements were tested in multiple transformation vector configurations. Each transformation vector was used to produce multiple R0 plants with each R0 plant representing a unique transgenic event made using the same transformation vector. Data for three different transformation vector configurations are provided as Tables 11 and 12.

Twelve mts-siRNA target elements were tested in a first vector configuration (A) with the results shown in Table 11. Surprisingly, the percentage of plants showing vegetative glyphosate tolerance ranged from 80-100%, but the percentage showing complete glyphosate-induced male sterility (induced male sterility included both non-viable pollen and no pollen production) ranged from 0-100%. See Table 11. For example, plants produced using a transformation vector containing mts-siRNA target element encoded by SEQ ID NO: 13, SEQ ID NO: 14, or SEQ ID NO: 15 had high numbers showing vegetative glyphosate tolerance (ranging from 90-100% of the plants tested), but none of the transgenic events showed complete glyphosate-induced male sterility; plants produced using a transformation vector containing mts-siRNA target element encoded by SEQ ID NO: 5 or SEQ ID NO: 9 had high numbers showing vegetative glyphosate tolerance (ranging from 90-100% of the plants tested) and moderate numbers showing glyphosate-induced male sterility (ranging from 50-40% of the plants tested); and plants produced using a transformation vector containing mts-siRNA target element encoded by SEQ ID NO: 2, SEQ ID NO: 7, or SEQ ID NO: 8 had high numbers showing vegetative glyphosate tolerance (ranging from 88-100% of plants tested) and high numbers showing glyphosate-induced male sterility (82-100% of the plants tested). Pollen development was assessed by Alexandar staining. Plants containing four events made with the transformation vector containing mts-siRNA target element provided as SEQ ID NO: 2 and sprayed with glyphosate to induce male-sterility showed very few aborted pollen grains or no pollen grains were detected. Plants that did not receive glyphosate application had normal pollen. See FIG. 4.

TABLE 11

Evaluation of R0 plants.

| SEQ ID NO: | Vector Configuration | Number of Plants Sprayed | % Vegetative Tolerant | % Completely Male-sterile | % No Pollen |
|---|---|---|---|---|---|
| 2 | A | 11 | 100 | 82 | 82 |
| 3 | A | 10 | 90 | 10 | 0 |
| 4 | A | 7 | 86 | 7 | 0 |
| 5 | A | 10 | 90 | 50 | 0 |
| 6 | A | 9 | 90 | 82 | 0 |
| 7 | A | 9 | 88 | 100 | 44 |
| 8 | A | 10 | 90 | 100 | 50 |
| 9 | A | 10 | 100 | 40 | 0 |
| 13 | A | 7 | 100 | 0 | 0 |
| 14 | A | 10 | 90 | 0 | 0 |
| 15 | A | 10 | 90 | 0 | 0 |
| 16 | A | 10 | 80 | 50 | 0 |

Four other mts-siRNA target elements were tested in a second and third vector configuration (B and C, respectively) with the results shown in Table 12. Differences in both the percentage of plants showing vegetative glyphosate tolerance and the percentage showing complete glyphosate-induced male sterility were observed between the two vector configurations. Vector configuration B provided an increased percentage of plants showing vegetative glyphosate tolerance for all of the mts-siRNA target elements tested. For the percentage showing complete glyphosate-induced male sterility, two of the mts-siRNA target elements (SEQ ID NO: 10 and SEQ ID NO: 11) tested performed better in vector configuration C, one of the mts-siRNA target elements (SEQ ID NO: 12) performed better in vector configuration B, and one of the mts-siRNA target elements (SEQ ID NO: 1) provided 100% complete glyphosate-induced male sterility in both configurations B and C.

TABLE 12

Evaluation of R0 plants

| SEQ ID NO: | Vector Configuration | Plants Sprayed | % Vegetative Tolerance | % Completely Male-sterile | % No Pollen |
|---|---|---|---|---|---|
| 1 | B | 9 | 67 | 100 | 100 |
| 10 | B | 10 | 90 | 55 | 22 |
| 11 | B | 2 | 100 | 50 | 0 |
| 12 | B | 10 | 100 | 50 | 20 |
| 1 | C | 13 | 38 | 100 | 60 |
| 10 | C | 6 | 83 | 100 | 0 |
| 11 | C | 9 | 55 | 80 | 0 |
| 12 | C | 15 | 87 | 23 | 0 |

Of the plants showing vegetative glyphosate tolerance, the percentage of glyphosate-induced male-sterile plants with no viable pollen ranged from 0-100%. For plants produced using a transformation vector that had greater than 60% of plants tested showing vegetative glyphosate tolerance and complete glyphosate-induced male sterility, the percentage of plants with no viable pollen ranged from 0-100%. Two mts-siRNA target elements (SEQ ID NO: 1 in vector configuration B and SEQ ID NO: 2 in vector configuration A) had 100% and 82% no viable pollen, respectively. These two mts-siRNA target elements (SEQ ID NO: 1 and SEQ ID NO: 2) differ by one nucleotide and are derived from the same cDNA sequence (SEQ ID NO: 17).

Example 4: Immunolocalization of CP4-EPSPS Protein in Tassel

Immunolocalization of CP4-EPSPS protein in tassel of transgenic plants was used to analyze protein expression at the cell and tissue level to confirm loss of CP4-EPSPS protein expression in pollen due to the presence of an operably linked mts-siRNA target element. R3 generation transgenic plants containing the cp4-epsps transgene operably linked to SEQ ID NO: 1 or as a control the cp4-epsps transgene without an operably linked mts-siRNA target element were grown in the greenhouse. The plants were sprayed with 1× glyphosate (0.75 lb ae/acre) at the V2 stage to confirm vegetative tolerance. Tassels at 1 cm to 17 cm were harvested at the V8 to V12 stages when anther tissue would be at the microspore mother cell and free microspore stages. Anthers were removed from the tassel spikelet using dissecting forceps and immediately fixed in 3.7% formaldehyde in phosphate buffered saline (PBS) under gentle vacuum. After washing in PBS, tissues were placed in embedding medium and frozen immediately. Frozen tissue blocks were stored at −80° C. until sectioned in −20° C. microtome and collected on charged slides.

Tissue sections were blocked with blocking agent (10% normal goat serum, 5% bovine serum albumin, 0.1% Triton X-100 in PBS) for two hours. Sections were incubated with anti-CP4-EPSPS antibody (1/500 in PBS). After washing the sections three times in PBS, tissue sections were incubated with the secondary antibody, goat anti-mouse IgG conjugated with Alexa Flour® 488 (Invitrogen, Eugene, Oreg.). A negative control was prepared by omitting the CP4-EPSPS antibody incubation. Both primary and secondary antibodies were incubated at room temperature for two to four hours and then further incubated overnight at 4° C. After washing, the tissues were imaged with Zeiss Laser Scanning Microscope (LSM) 510 META confocal microscope using a 488 nm laser for excitation and 500-550 nm (green channel) for emission filter set. The same imaging parameter was applied throughout the samples including controls. Fluorescent and bright field images were scanned from each section, and merged using LSM software afterward to show structural information. The data for the negative controls showed the expected absence of signal. The data for transgenic plants containing the cp4-epsps transgene operably linked to SEQ ID NO: 1 showed a low fluorescence signal indicating low CP4-EPSPS protein expression in the anther wall, tapetum, and developing pollen microspores of the anther. The data for the control transgenic plants (those containing the cp4-epsps transgene without an operably linked mts-siRNA target element) showed a high fluorescence signal indicating high CP4-EPSPS protein expression in the anther wall, tapetum, and developing pollen microspores of the anther.

The loss of CP4-EPSPS protein expression in pollen in plants containing the cp4-epsps transgene operably linked to the mts-siRNA target element provided as SEQ ID NO: 1 correlates with the observed complete glyphosate-induced male sterility in these plants. This data confirmed that the observed complete glyphosate-induced male sterility is the result of loss of CP4-EPSPS protein expression in pollen due to the presence of the operably linked mts-siRNA target element provided as SEQ ID NO: 1.

Example 5: Field Trials

For optimal use in hybrid production it is desirable to have very low anther extrusion in field conditions after herbicide application combined with vegetative herbicide tolerance (as measured by low crop injury). Other aspects of hybrid corn production may also be desirable, such as plant height and yield. To assess this, transgenic plants comprising the cp4-epsps transgene operably linked to a mts-siRNA target element were tested at advanced generations in field conditions and multiple parameters were measured.

Field trials of R3 generation plants containing the cp4-epsps transgene operably linked to the mts-siRNA target element provided as SEQ ID NO: 1 were conducted at multiple locations to assess vegetative glyphosate tolerance and tassel-specific glyphosate sensitivity. The field trials tested R3 generation plants containing the same transgenic insert at different genomic locations. The plants tested contained a single copy of one of four unique transgenic events created using the same plant transformation vector containing the cp4-epsps transgene operably linked to the mts-siRNA target element provided as SEQ ID NO: 1. Trials were conducted using a randomized complete block design. Multiple trait efficacy and agronomic parameters were scored throughout the field trial season, and at the end of the season yield was determined. Trait efficacy field trials were conducted by applying glyphosate herbicide at 0.75 lb ae/acre at V7 followed by 0.75 lb ae/acre at V9 and rating crop injury percentage at the VT stage (CIPVT), average anther extrusion percentage at the S90+8 stage (AES9E), and yield (measured as bushels per acre (bu/acre)) at the end of the season. The field trials included the glyphosate tolerant transgenic event NK603 (ATCC deposit number PTA-24780) as a negative control for glyphosate-induced male sterility and as a positive control for vegetative tolerance to glyphosate. Plants containing the NK603 event exhibit commercial level vegetative glyphosate tolerance and produce fully glyphosate tolerant tassel. All data were subjected to analysis of variance and mean (LSD) separated at $p<0.05$.

TABLE 13

Trait efficacy results for field trials with plants containing SEQ ID NO: 1

| Event | CIPVT | AES9E |
|---|---|---|
| NK603 control | 1.25 | 95.00 |
| Event 1 | 1.25 | 0 |
| Event 2 | 3.75 | 3.25 |
| Event 3 | 0 | 4.00 |
| Event 4 | 0 | 1.75 |

The average crop injury at the VT stage for the control plants containing the NK603 event was 1.25. The average crop injury for plants containing Event 1, Event 2, Event 3, and Event 4 was 1.25, 3.75, 0, and 0, respectively. The crop injury least significant difference (LSD) at 0.05 was 10.25 for all events tested. These results indicate that plants containing the four transgenic events containing the mts-siRNA target element SEQ ID NO: 1 had zero to very low vegetative injury with the application of 0.75 lb ae/acre of glyphosate at V7 followed by V9, similar to control plants containing the NK603 event.

The average anther extrusion at the S90+8 stage for the control plants containing the NK603 event was 95. The average anther extrusion at S90+8 for plants containing Event 1, Event 2, Event 3, and Event 4 was 0, 3.25, 4, and 1.75, respectively. The average anther extrusion at S90+8 LSD at 0.05 was 42.71 for all events tested. These results indicate that plants containing the four transgenic events containing the mts-siRNA target element SEQ ID NO: 1 had zero to very low anther extrusion with the application of 0.75 lb ae/acre of glyphosate at V7 followed by V9 in contrast to control plants containing the NK603 event, which were fully male-fertile following glyphosate application.

At the end of the season the maize was harvested from these field trials and yield was determined. The average yield for the control plants containing the NK603 event was 96.74 bu/acre. The average yield for plants containing Event 1, Event 2, Event 3, and Event 4 was 102.17 bu/acre, 96.48 bu/acre, 97.59 bu/acre, and 95.8 bu/acre, respectively. The yield LSD at 0.05 was 26.25 bu/acre for all events tested. See Table 14. These results indicate that plants containing the four transgenic events containing the mts-siRNA target element SEQ ID NO: 1 had yield parity with NK603.

TABLE 14

Yield results for field trials with plants containing SEQ ID NO: 1

| Event | Average yield (bu/acre) |
|---|---|
| NK603 Control | 96.74 |
| Event 1 | 102.17 |
| Event 2 | 96.48 |
| Event 3 | 97.59 |
| Event 4 | 95.8 |

Field trials of R2 or higher generation inbred plants containing the cp4-epsps transgene operably linked to various mts-siRNA target elements were conducted at multiple locations to assess vegetative glyphosate tolerance and tassel-specific glyphosate sensitivity. The field trials tested R2 or higher generation inbred plants containing a single copy of the cp4-epsps transgene operably linked to the mts-siRNA target element SEQ ID NO: 1, SEQ ID NO: 4, SEQ ID NO: 5, SEQ ID NO: 6, SEQ ID NO: 7, or SEQ ID NO: 8, each in transformation vector configuration A. Trials were conducted using a group block design with the grouping factor being either the transformation vector, or a group of transformation vectors if event numbers for a specific transformation vector were low. Multiple trait efficacy and agronomic parameters were scored throughout the field trial season, and at the end of the season yield was determined. Trait efficacy field trials were conducted by applying a glyphosate at 1.5 lbs ae/acre applied to V2 corn followed by glyphosate at 0.75 lbs ae/acre applied to V8 corn (875 growing degree days) followed by glyphosate at 0.75 lbs ae/acre applied to V10 corn (1025 growing degree days). Ratings of crop injury percentage at the VT stage (CIPVT), average anther extrusion percentage at the S90+8 stage (AES90+8), average plant height (in inches), and yield (measured as bushels per acre (bu/acre)) at the end of the season. The field trials included the glyphosate tolerant transgenic event NK603 as a negative control for glyphosate-induced male sterility and as a positive control for vegetative tolerance to glyphosate. A glyphosate tolerant mix of male pollinators consisting of three hybrid germplasm backgrounds was placed every third plot and surrounding the entire trial to serve as the pollen source for test entries. Herbicide treatments were applied using a $CO_2$ backpack or tractor mounted sprayer calibrated to deliver 15 gallons per acre (GPA) using air-inducted Teejet® TTI nozzles (TeeJet Technologies, Springfield, Ill.) with water as the herbicide carrier. All data were subjected to analysis of variance and mean (LSD) separated at $p<0.05$. Results are provided in Table 15.

No significant difference in crop injury percentage at VT (CIPVT) or in average plant height compared to the control NK603 was seen for the plants tested containing mts-siRNA target element SEQ ID NO: 1, SEQ ID NO: 4, SEQ ID NO: 5, SEQ ID NO: 6, SEQ ID NO: 7, or SEQ ID NO: 8. The plants containing mts-siRNA target element SEQ ID NO: 1, SEQ ID NO: 5, SEQ ID NO: 6, or SEQ ID NO: 7 also had no significant decrease in seed yield compared to the control NK603. Plants containing the mts-siRNA target element SEQ ID NO: 1 or SEQ ID NO: 7 had very low or no anther extrusion with AES90+8 values of 0-2.75% and 0-1.5%, respectively. Plants containing the mts-siRNA target element SEQ ID NO: 4, SEQ ID NO: 5, SEQ ID NO: 6, or SEQ ID NO: 8 had significantly decreased anther extrusion compared to control plants, with AES90+8 values ranging from 10% to 25%.

TABLE 15

Different mts-siRNA in same transformation vector configuration A

| SEQ ID NO: | # events tested | CIPVT (LSD = 8.1) | AES90+8 (LSD = 10) | Seed Yield bu/acre (LSD = 24.7) | Avg. plant height (inches) (LSD = 6.9) |
|---|---|---|---|---|---|
| n/a | NK603 | 0-6.25% | 90% | 110 | 83.2 |
| 1 | 8 | 2.5-6.25% | 0-2.75% | 97-99 | 84.75 |
| 4 | 4 | 1.25-3.75% | 16.25-18.75% | 70-80 | 85.1 |
| 5 | 4 | 5% | 10%-20% | 90-100 | 84.31 |
| 6 | 7 | 3.75% | 25% | 120 | 82.1 |
| 7 | 2 | 3.75-5% | 0-1.5% | 100-110 | 79.8 |
| 8 | 2 | 2.5-2.7% | 15.75-17.85% | 80-90 | 80.1 |

Example 6: Hybrid Seed Production

Transgenic plants and seeds of the invention may be used for breeding purposes including in hybrid seed production. Transgenic maize plants comprising a recombinant DNA construct comprising a transgene encoding a glyphosate-tolerant EPSPS protein operably linked to a mts-siRNA target element are planted in an area, such as an open field. Other parent maize plant(s) may or may not be present in the same area. For weed control during seed production, glyphosate may be applied to the transgenic maize plants at vegetative stages as directed on Roundup® agricultural product labels.

Hybrid seed production may be conducted by applying glyphosate to the transgenic maize plants (female) beginning just prior to or during tassel development at maize vegetative growth stages ranging from V7 to V13. The glyphosate application will produce an induced male-sterile phenotype through tissue-selective glyphosate tolerance in the transgenic maize plants. The induced male-sterile transgenic maize plants may be pollinated by other pollen donor plants (male), resulting in viable hybrid maize seed carrying the recombinant DNA construct for tissue-selective glyphosate tolerance. The pollen donor plants may or may not be present in the same area and may or may not be transgenic maize plants. Pollination may be accomplished by any means known in the art, including by proximity placement of plants or by hand pollination. Hybrid seed is harvested from the transgenic maize plants.

Having illustrated and described the principles of the present invention, it should be apparent to persons skilled in the art that the invention can be modified in arrangement and detail without departing from such principles. We claim all modifications that are within the spirit and scope of the appended claims.

What is claimed is:

1. A recombinant DNA molecule comprising an mts-siRNA target element comprising SEQ ID NO: 1, or SEQ ID NO: 2, or full-length complements thereof wherein the mts-siRNA target element is operably linked to a heterologous transcribable polynucleotide molecule.

2. The recombinant DNA molecule of claim 1, wherein the heterologous transcribable polynucleotide molecule encodes a protein that confers herbicide tolerance in plants.

3. The recombinant DNA molecule of claim 2, wherein said heterologous transcribable polynucleotide molecule encodes a glyphosate-tolerant 5-enolypyruvyl shikimate 3-phosphate synthase (EPSPS).

4. A method of producing a recombinant DNA molecule, said method comprising operably linking an mts-siRNA target element comprising SEQ ID NO: 1 or SEQ ID NO: 2, or full-length complements thereof to a heterologous transcribable polynucleotide molecule.

5. A transgenic plant or part thereof comprising in its genome the recombinant DNA molecule of claim 1.

6. A seed of the transgenic plant of claim 5, comprising said DNA molecule.

7. The plant of claim 5, wherein said plant is a monocotyledonous plant.

8. The plant of claim 7, wherein said plant is a maize plant.

9. A method of selectively regulating the expression of a protein in a male reproductive tissue of a transgenic plant comprising expressing in said transgenic plant the recombinant DNA molecule of claim 1.

10. The method of claim 9, wherein said protein comprises a glyphosate-tolerant 5-enolypyruvyl shikimate 3-phosphate synthase (EPSPS).

11. A method of inducing male-sterility in a transgenic plant comprising:
   a) growing a transgenic plant comprising the recombinant DNA molecule of claim 1, wherein the heterologous transcribable polynucleotide molecule encodes a protein conferring tolerance to at least a first herbicide; and
   b) applying an effective amount of said herbicide to said transgenic plant, wherein the herbicide application is carried out prior to or concurrently with development of the male reproductive tissue of said transgenic plant, thereby inducing male-sterility in the transgenic plant.

12. The method of claim 11, wherein said heterologous transcribable polynucleotide molecule encodes a glyphosate-tolerant 5-enolypyruvyl shikimate 3-phosphate synthase (EPSPS).

13. The method of claim 11, wherein said herbicide is glyphosate.

14. The method of claim 13, wherein said effective amount of herbicide is about 0.125 pounds acid equivalent per acre to about 8 pounds acid equivalent per acre of glyphosate.

15. The method of claim 11, wherein said effective amount of herbicide is applied at a developmental stage selected from the group consisting of the V4, V5, V6, V7, V8, V9, V10, V11, V12, V13, and V14 stage.

16. A method of producing hybrid seed comprising:
   a) applying an effective amount of herbicide to a transgenic plant comprising the recombinant DNA molecule of claim 1, wherein the heterologous transcribable polynucleotide molecule encodes a protein conferring tolerance to at least a first herbicide, and wherein said herbicide application is carried out prior to or concurrently with development of the male reproductive tissue of the transgenic plant, thereby inducing male-sterility in said transgenic plant;
   b) fertilizing said transgenic plant with pollen from a second plant; and
   c) allowing hybrid seed to form from said transgenic plant.

17. The method of claim 16, wherein said fertilizing comprises allowing wind pollination to occur.

18. The method of claim 16, wherein said heterologous transcribable polynucleotide molecule encodes a glyphosate-tolerant 5-enolypyruvyl shikimate 3-phosphate synthase (EPSPS).

19. The method of claim 16, wherein said herbicide is glyphosate.

20. The method of claim 19, wherein said glyphosate is applied concurrently with development at an effective amount of about 0.125 pounds acid equivalent per acre to about 8 pounds acid equivalent per acre.

21. A hybrid seed produced by the method of claim 16, wherein the hybrid seed comprises said recombinant DNA molecule.

* * * * *

SEQUENCE LISTING

```
<160> NUMBER OF SEQ ID NOS: 93

<210> SEQ ID NO 1
<211> LENGTH: 201
<212> TYPE: DNA
<213> ORGANISM: Artificial Sequence
<220> FEATURE:
<223> OTHER INFORMATION: Synthetic sequence

<400> SEQUENCE: 1
agacgacgac cgtgcatggt gatgaatcac agacgacgaa cacgcatgtc gcatcgccgt      60
cctctttgta tcacacagca tcaccttctt cgctctacta ctcccccgag caatcaccga     120
ccaataacac caaccatcaa cctcccccgt cgccgccgcc ttcaccgtcc tcccctcaca     180
ccatagaact gcaaatgtcc g                                               201

<210> SEQ ID NO 2
<211> LENGTH: 201
<212> TYPE: DNA
<213> ORGANISM: Artificial Sequence
<220> FEATURE:
<223> OTHER INFORMATION: Synthetic sequence

<400> SEQUENCE: 2
agacgacgac cgtgcatggt gatgaatcac agacgacgaa cacgcatgtc gcatcgccgt      60
cctctttgaa tcacacagca tcaccttctt cgctctacta ctcccccgag caatcaccga     120
ccaataacac caaccatcaa cctcccccgt cgccgccgcc ttcaccgtcc tcccctcaca     180
```
ccatagaact gcaaatgtcc g                                              201

<210> SEQ ID NO 3
<211> LENGTH: 195
<212> TYPE: DNA
<213> ORGANISM: Zea mays

<400> SEQUENCE: 3
tctagccaca cggtcacgtt tggacgacca ataataggct tgcaacccett caaattgtgt    60 ccatcagctt cccaacgtgc atatcgccat cctctgcttc gtgtcccatg tcaccacccc   120
cactcttcct ctttacatgc aatgcaaata aagcagatcc aacgtggatg agggtgaatc   180
ggatgttgag gtggg                                                     195

<210> SEQ ID NO 4
<211> LENGTH: 221
<212> TYPE: DNA
<213> ORGANISM: Zea mays

<400> SEQUENCE: 4
acgagggaat gtcattggtc gatgagttgg aggcgtcaaa tgcagataaa gctacaactt    60
ccatgtggag gatgactgcg acgttgtggc agactcatcc actacagtga gagtctagga   120
aagcatgaag ccgattgtgg acatcgatgt cggtgtcaag gacttataga tgtcatgttg   180
ggagagcaac catggcacga tagttaaggc gcaagggtat c                        221

<210> SEQ ID NO 5
<211> LENGTH: 108
<212> TYPE: DNA
<213> ORGANISM: Zea mays

<400> SEQUENCE: 5
tggctgcttc tgttggcgtg aaagctcgag tgctcctaaa tggtcgtcgt attagctgat    60
acgacatcta cccgatgcaa tagataatat tgtttacacg cgtgagtc                108

<210> SEQ ID NO 6
<211> LENGTH: 108
<212> TYPE: DNA
<213> ORGANISM: Zea mays

<400> SEQUENCE: 6
tcgccgagaa gggagtagta gtattacctg atatctatgc taattcaggt ggtgtggtcg    60
ttagctactt taattgagtg ggttcagaac attcaaggtt tcatgtgg                108

<210> SEQ ID NO 7
<211> LENGTH: 206
<212> TYPE: DNA
<213> ORGANISM: Zea mays

<400> SEQUENCE: 7
ggaaccggtg accagctgca cgacgatgaa tcctacaaga cgaccatgta atacacagtg    60
tcgtcctctt cgttctacta ctcaacagag cagtcgccga ccaataacga atggagtatt   120
atctctgtcc ttcaccttac accatattca caccatagaa ctgcaaatgt ccgaggtacc   180
aactaacatc ggtacctttg gcatga                                         206

<210> SEQ ID NO 8
<211> LENGTH: 195
<212> TYPE: DNA
<213> ORGANISM: Zea mays

<400> SEQUENCE: 8

```
agattggtca tacactagat agggctagat cactcgggtc gccacaagtt gaagaatgca    60
aagagtgtcc acatgatttc atggtgatga acagtgattt tatgagcaaa ctagcaaagg   120
ataatcagtt gcatatatgt gatgaagacc gatcagtttc cgagcaaagt agcaaatgag   180
tcatcgaagc tgtca                                                    195
```

<210> SEQ ID NO 9
<211> LENGTH: 300
<212> TYPE: DNA
<213> ORGANISM: Zea mays

<400> SEQUENCE: 9

```
ggacaacaag caccttcttg ccttgcaagg cctcccttcc ctatggtagc cacttgagtg    60
gatgacttca ccttaaagct attgattccc taagtgccag acataatagg ctatacattc   120
tctctggtgg caacaatgag ccatttggt tggtgtggta gtctattatt gagttttttt    180
tggcaccgta ctcccatgga gagtagaaga caaactcttc accgttgtag tcgttgatgg   240
tattggtggt gacgacatcc ttggtgtgca tgcactggtg agtcactgtt gtactcggcg   300
```

<210> SEQ ID NO 10
<211> LENGTH: 90
<212> TYPE: DNA
<213> ORGANISM: Artificial Sequence
<220> FEATURE:
<223> OTHER INFORMATION: Synthetic sequence

<400> SEQUENCE: 10

```
agacgacgac cgtgcatggt gatgaatcac agacgacgaa cacgcatgtc gcatcgccgt    60
cctctcacac catagaactg caaatgtccg                                     90
```

<210> SEQ ID NO 11
<211> LENGTH: 165
<212> TYPE: DNA
<213> ORGANISM: Artificial Sequence
<220> FEATURE:
<223> OTHER INFORMATION: Synthetic sequence

<400> SEQUENCE: 11

```
agacgacgac cgtgcatggt gatgaatcac agacgacgaa cacgcatgtc gcatcgccgt    60
cctctcacac catagaactg caaatgtccg acaacaagca ccttcttgcc ttgcagtatt   120
ggtggtgacg acatccttgg tgtgcatgca ctggtgagtc actgt                   165
```

<210> SEQ ID NO 12
<211> LENGTH: 170
<212> TYPE: DNA
<213> ORGANISM: Artificial Sequence
<220> FEATURE:
<223> OTHER INFORMATION: Synthetic sequence

<400> SEQUENCE: 12

```
agacgacgac cgtgcatggt gatgaatcac agacgacgaa cacgcatgtc gcatcgccgt    60
cctctcacac catagaactg caaatgtccg ctcttcaccg ttgtagtcgt tgatggtatt   120
ggtggtgacg acatccttgg tgtgcatgca ctggtgagtc actgttgtac              170
```

<210> SEQ ID NO 13
<211> LENGTH: 82
<212> TYPE: DNA

<213> ORGANISM: Artificial Sequence
<220> FEATURE:
<223> OTHER INFORMATION: Synthetic sequence

<400> SEQUENCE: 13

```
acgtgataac ttctatgctg gctgtgattg ctagttgaag aaaagaatag atatggtgac        60
atcaagtttc cactgcgtga cg                                                 82
```

<210> SEQ ID NO 14
<211> LENGTH: 106
<212> TYPE: DNA
<213> ORGANISM: Artificial Sequence
<220> FEATURE:
<223> OTHER INFORMATION: Synthetic sequence

<400> SEQUENCE: 14

```
cccaacgtgc atatcgccat cctctgctac gagggaatgt cattggtcga tgagatgagg        60
gtgaatcgga tgttgaggtg gcacgatagt taaggcgcaa gggtat                      106
```

<210> SEQ ID NO 15
<211> LENGTH: 80
<212> TYPE: DNA
<213> ORGANISM: Artificial Sequence
<220> FEATURE:
<223> OTHER INFORMATION: Synthetic sequence

<400> SEQUENCE: 15

```
tcgtccaaac gtgaccgtgt ggctagaagc agaggatggc gatatgcacg ttatgctttc        60
ctagactctc actgtagtgg                                                    80
```

<210> SEQ ID NO 16
<211> LENGTH: 264
<212> TYPE: DNA
<213> ORGANISM: Artificial Sequence
<220> FEATURE:
<223> OTHER INFORMATION: Synthetic sequence

<400> SEQUENCE: 16

```
gacaacaagc accttcttgc cttgcagtat tggtggtgac gacatccttg gtgtgcatgc        60
actggtgagt cactgttgta cgtgataact tctatgctgg ctgtgattgc tagttgaaga       120
aaagaataga tatggtgaca tcaagtttcc actgcgtgac gccaacgtgc atatcgccat       180
cctctgctac gagggaatgt cattggtcga tgagatgagg gtgaatcgga tgttgaggtg       240
gcacgatagt taaggcgcaa gggt                                              264
```

<210> SEQ ID NO 17
<211> LENGTH: 1826
<212> TYPE: DNA
<213> ORGANISM: Zea mays

<400> SEQUENCE: 17

```
atcgcttgct cgctcgttgc ttttggcagg tatagcaagc acaccccggc cttcacccat        60
cgagcctcag ttagcatctc tagctagctc ttctccacgt ttagctttca ataatccatc       120
gtctctgcag gtagccagca gacaccactt cacaagcagg atggcaatga actggttgtt       180
gttttgccag ggtcccagcc ctatgaaagc gcgttacgtt tacgcagtgc tctttctgct       240
ggccaacttg tctgcgtggc tcacgcgaga gaaccgtata tcatattact tagcgcagcg       300
gggcaacgcc cgctgtcacg gtgaccgggg ctgtctcgcg gctcagatgg tgctgacaat       360
tagccatact ttctgtatgt ttttcgtggc catgctaata tccaccgtga ccacgtccaa       420
```

```
gttgaatgac cgcagaaatt catggcactg cgggtggtgg ccggtgaagg ttgccctttt    480
tgtaggttgt ttcttcttct ctcaggtggt tccatccggt tggatcgaaa cctacgggaa    540
aattgcgcag gttggagcag gggtatttct tgtacttcag cttatgtcta ccataagatt    600
tatcacacag ctgaattaca aattatgcga gaccaatttt gaagaaaggt acatccgtgt    660
cttcgcaatc tctgttactg ccatcctcac attttttggga ttgatagtat tcttgagcct    720
aaagtttgcc gagtgttggc acaatatgga gctcattgtc atcacaatgg tgctattttt    780
catcatgtgt gtagtctcac taatgtccaa ggctaacaaa ttttttcatgg agcctgcatt    840 aattggtggg tacgctactt tcatatgcct gctagcgatt acaagtgaac ctgagtcagg    900
atgcgacatg aaacgcaaag caggtccagg tgctggttgg ttaaccatttt cctttttttgt    960 ttctggactc ctcggcactg tttattctgc ttttactatg ggcatcggct acaaatgtac   1020
acgaaacacg ttggagtcgg aagacaatgt accatatggg tacggttttt ttcatttcat   1080
cttcatgtcg ggctgcatgt actttggaat gatgtttgtt gcctgggaca cacatcatac   1140
catggaagat aacgatactg ctggccagaa ttttgggagt aggctggctc caacacttcc   1200
tcgcagagat ctttggaaca gatgaccagc tgcacggcga tgaatcccat acgacgaccg   1260
tgcatggtga tgaagccgag acgacgaccg tgcatggtga tcaagccgag acgacgaccg   1320
tgcatgttga tgaagccgag acgacgaccg tgcatggtga tcaagccgag acgacgactg   1380
tgcatggtga tgaatccgag actacgaccg tgcatggtga tgaatccgag acgacgaccg   1440
tgcatggtga tgaatcacag acgacgaaca cgcatgtcac atcgccgtcc tctttgtatc   1500
acacagcgtc gccctcttcg ctctactact cccccgagca tcaccgacca ataacattga   1560
ccatcaacct cctccgtcgc cgccgcgttc accgtcctcc cctcacacca tagaactgca   1620
aatgtccgag ataccaaata tcggtacatc tggcatgaat gaagaggagg acgatgatga   1680
ctatattaga gaatgggaga gtgaatatat ggtcgctccg taattaacaa cttgtatttc   1740
gacatccact agtagaaaag agctctaagg cggggcactg gcggttcact taactgaacc   1800
gtcagtggaa aaaaaaaaa aaaaaa                                         1826
```

<210> SEQ ID NO 18
<211> LENGTH: 757
<212> TYPE: DNA
<213> ORGANISM: Zea mays

<400> SEQUENCE: 18

```
atctagtagt tgataactat gaggtttgat aactaggagg ttcggcatgg gtacatgtat     60
tgtcattatt gtttgtcgcg agtacctttg taaatttaga aatgagtcta accatatttt    120
cttagttatg tgtgagatac tggaggccac caaagctaga aatacgttga ttactatata    180
ttaatgcaga gcatggagca aagctgatct tttaaaatat acatgttacc tccttatttc    240
tagccacacg gtcacgtttg gacgaccaat aataggcttg caaccccttca aattgtgtcc    300 atcagcttcc caacgtgcat atcgccatcc tctgcttcgt gtcccatgtc accacccca    360 ctcttcctct ttacatgcaa tgcaaataaa gcagatccaa cgtggatgag ggtgaatcgg    420
atgttgaggt ggggtctgct aaatctccca aataatcaaa tggcggctgc aacaacacga    480
gggaatgtca ttggtcgatg agttggaggc gtcaaatgca gataaagcta caacttccat    540
gtggaggatg actgcgacgt tgtggcagac tcatccacta cagtgagagt ctaggaaagc    600
atgaagccga ttgtggacat cgatgtcggt gtcaaggact tatagatgtc atgttgggag    660
```

```
agcaaccatg gcacgatagt taaggcgcaa gggtatctgt aatactcaaa attgtataca    720
aggaatatat agaggtcttc tcaaaaaaaa aaaaaaa                              757
```

<210> SEQ ID NO 19
<211> LENGTH: 820
<212> TYPE: DNA
<213> ORGANISM: Zea mays

<400> SEQUENCE: 19

```
atgcgctacg gcagtttgta gtttagtcta atcaagccat ggtgttgaaa cttgaccata     60
cttgtctcaa tgagactttg gagtgaacca aatgagctta tgttcttata tgactactag    120
ctagaagtta gagcctagat gatggctgct tctgttggcg tgaaagctcg agtgctccta    180
aatggtcgtc gtattagctg atacgacatc tacccgatgc aatagataat attgtttaca    240
cgcgtgagtc caaaattgtt ggctttgggt cggagcagtt aatgcgagaa gtgtatttta    300
tcacttctga gtgcaacctt ttttttatta tttttccgag cttctgcctc ttgcatatgt    360
tgtagattct cgccgagaag ggagtagtag tattacctga tatctatgct aattcaggtg    420
gtgtggtcgt tagctacttt aattgagtgg gttcagaaca ttcaaggttt catgtgggcc    480
gaggagaaag tggacgatga actagaaaag gacatgagca gtgcttttca acacatgaag    540
gccatgtgca aatctttggt gctgccgaag tgtgtcgtga cattggaatt gcgggtctag    600
aaaaacaagc tcattagatt tctgaaaaaa cattagaagt tattagattg gtagcatttt    660
tttaagattt aaaatttat agaagtcatc attttcgttt attggaagaa atattttggg   720
aagttgaaaa gatgctctaa catccaacca cgcaaactat cttgcaacca ctctaacacg    780
atttcggtaa tatgttttta tgaaaaaaaa aaaaaaaaaa                          820
```

<210> SEQ ID NO 20
<211> LENGTH: 1814
<212> TYPE: DNA
<213> ORGANISM: Zea mays

<400> SEQUENCE: 20

```
gcctcagatg ctagctagct cttctccacg tttagcttcc aatccgtcca tctctctgca     60
gactgcaggt gagcgccata tctatctcaa tcaatctgaa gctagtaatt tgttttatac    120
aaatctacaa gtaatcgatc atcagttaac atatgatgtc gatctgtgtt gtatttgggt    180 gaacagggt atttcttgta gttcagctca tgagtttcac aagacttcat cacacggtta    240
aactacaaat tgtgcgagac aaattaggta tgtatgttta ccactgtttt aatcgatcta    300
acttagaaaa cgtgtgttca acgtacgagt gactgtcaag ccgatggttg gctttgattg    360
tgtgtgttcg aaacctaatc atgcatggca tgccgaacaa attttggttg gatgcatata    420
tatatgctag gacatctgag gatcatatgt gccaaatagt ttagccaatt aatttctcac    480
aagcacgcag attcagcagt tggatcaaac ttgagaaaca ccattttgtt tgattcgttc    540
tcatatctgc ggagttgcta gctagttgtt cttggcattg gtagtttgag aacgaatgtc    600
cttagaacat cccgagtaat ttatagtgtg caaagtttga gatccgctgg gtttaatctg    660
agttagtttt gatcttttaga tcaattttta aggtgctatt cgtcaatatt ggatggtccg    720
gatcgaataa attctagtgg tcccatatga agacctttga atttcgtcca gcagattcct    780
tatggcggcc ttgtgactat attgttcgta gtttatgatt tttagacacc atttgatagg    840
gttttgagat tttcacctaa aactcctcat gctgaaaact gttgggttga tttgtcatac    900
cgggaggtct gatattcata ccggaggatg aggtctattt tactcagcct tttgagagtc    960
```

```
ttttactgat tcttctcctc ctcaattctg gcattttctg ctgtgttttt ttaaaattat    1020
tactgagtac atctccccac aaagttagcg tgtgtatagt cattgtcttt tttatatgta    1080
actgcgtggg attgaataaa aaatataag ccaaaatcac ctagagtgaa tatttgttgg    1140
ctcttattca agttcttttg atcgtctgct tgctctaatc catgcataca ccaaatttta    1200
ttttgtcttt acgctgcaaa caaaaaccaa ctatatgcat tacatatgtt gtgtgtatta    1260
tgctggctta tattaatatt tgcgtttaca gtagcgatac tgttgaccag aattttggaa    1320
ataaaccggc tccaacacct acttgcaaag atatttggaa ccggtgacca gctgcacgac    1380
gatgaatcct acaagacgac catgtaatac acagtgtcgt cctcttcgtt ctactactca    1440
acagagcagt cgccgaccaa taacgaatgg agtattatct ctgtccttca ccttacacca    1500
tattcacacc atagaactgc aaatgtccga ggtaccaact aacatcggta cctttggcat    1560
gaatgatgaa tgaagaggac ggcgatgact atattagaga atgggaaagt gaataactgc    1620
tcgatctgtc actaacaatt tgtaattcaa catcagaggc atattaattt cgtttatgaa    1680
acgttgtaat atagacgtgc ctacggtggc gtcacgtttg atgtatggat atgtttgaca    1740
tagtaagaca tgtttcatgt gtattctttt atccatacta ctcttaaaga aatacatgta    1800
tgctgatgga tgaa                                                    1814

<210> SEQ ID NO 21
<211> LENGTH: 679
<212> TYPE: DNA
<213> ORGANISM: Zea mays

<400> SEQUENCE: 21
atgctgagca acaaagtttt acgaacatgt gaagaggaga taaaattggg catcacaatt     60
gcgtgtgcaa atgtttatgg ttcgatccat ataggattgg taggcattag gaactcagat    120
atgtctgggc ttctacatca cagggaatgg gtggaatcaa ttcgtgggtc acgccagaaa    180
agagttgtgg acataattta tatatgtttg tgagctaaaa ataagtgttg gctaccattg    240
aagtatagat tggtcataca ctagataggg ctagatcact cgggtcgcca caagttgaag    300
aatgcaaaga gtgtccacat gatttcatgg tgatgaacag tgattttatg agcaaactag    360
caaaggataa tcagttgcat atatgtgatg aagaccgatc agtttccgag caaagtagca    420
aatgagtcat cgaagctgtc atctaggaca aactcgttgt tatcgtagat tagacaacaa    480
ggctaggaca tcatccttag tcgtcagatc aagcgatgaa caacaacatg gaattggaag    540
attaagataa aaggaatagt agatatataa tggtttggtt tgatattgga ttactcaatt    600
gattgtggtc ctctaatata taaagagtgg atagtattat cctagtagaa aacttttca    660 aaaaaaaaaa aaaaaaaaa                                                 679

<210> SEQ ID NO 22
<211> LENGTH: 631
<212> TYPE: DNA
<213> ORGANISM: Zea mays

<400> SEQUENCE: 22
aacttcatat agaccatagt tagtgacagc attaaagttt gagatgttga atgctaaaaa     60
acaattagtc acaatattgt ttagataaaa atttgagatg tcggaggaag ctgctgaaaa    120
aggttaactt tatctatggg actaagcttc aattcggcat cctcccattc ttcagtctta    180
atgtcgttgc cgccgagtac aacagtgact caccagtgca tgcacaccaa ggatgtcgtc    240
```

```
accaccaata ccatcaacga ctacaacggt gaagagtttg tcttctactc tccatgggag      300
tacggtgcca aaacaaactc aataatagac taccacacca accaaaatga ctcattgttg      360
ccaccagaga gaatgtatag cctattatgt ctggcactta gggaatcgat agctttaagg      420
tgaagtcatc cactcaagtg ctaccatag ggaagggagg ccttgcaagg caagaaggtg       480
cttgttgtcc gttgtgataa caccttttca acaataatgt tcatacctac attgttcgtt      540
cgtcgttggg taaaaacatt gctatatcta tttatttta ttatcatata tatattatta      600 atactttgt ttgccaaaaa aaaaaaaaaa a                                      631

<210> SEQ ID NO 23
<211> LENGTH: 22
<212> TYPE: DNA
<213> ORGANISM: Zea mays

<400> SEQUENCE: 23
catcaccatg cacggtcgtc gt                                               22

<210> SEQ ID NO 24
<211> LENGTH: 18
<212> TYPE: DNA
<213> ORGANISM: Zea mays

<400> SEQUENCE: 24
atcaccatgc acggtcgt                                                    18

<210> SEQ ID NO 25
<211> LENGTH: 18
<212> TYPE: DNA
<213> ORGANISM: Zea mays

<400> SEQUENCE: 25
acgaccgtgc atggtgat                                                    18

<210> SEQ ID NO 26
<211> LENGTH: 22
<212> TYPE: DNA
<213> ORGANISM: Zea mays

<400> SEQUENCE: 26
cgcatgtcac atcgccgtcc tc                                               22

<210> SEQ ID NO 27
<211> LENGTH: 22
<212> TYPE: DNA
<213> ORGANISM: Zea mays

<400> SEQUENCE: 27
cggacatttg cagttctatg gt                                               22

<210> SEQ ID NO 28
<211> LENGTH: 22
<212> TYPE: DNA
<213> ORGANISM: Zea mays

<400> SEQUENCE: 28
gacatttgca gttctatggt gt                                               22

<210> SEQ ID NO 29
<211> LENGTH: 20
<212> TYPE: DNA
<213> ORGANISM: Zea mays
```

```
<400> SEQUENCE: 29
ccgtgcatgg tgatgaatcc                                              20

<210> SEQ ID NO 30
<211> LENGTH: 19
<212> TYPE: DNA
<213> ORGANISM: Zea mays

<400> SEQUENCE: 30
caccatgcac ggtcgtcgt                                               19

<210> SEQ ID NO 31
<211> LENGTH: 22
<212> TYPE: DNA
<213> ORGANISM: Zea mays

<400> SEQUENCE: 31
acacgcatgt cacatcgccg tc                                           22

<210> SEQ ID NO 32
<211> LENGTH: 23
<212> TYPE: DNA
<213> ORGANISM: Zea mays

<400> SEQUENCE: 32
tagccacacg gtcacgtttg gac                                          23

<210> SEQ ID NO 33
<211> LENGTH: 24
<212> TYPE: DNA
<213> ORGANISM: Zea mays

<400> SEQUENCE: 33
agggtgaatc ggatgttgag gtgg                                         24

<210> SEQ ID NO 34
<211> LENGTH: 24
<212> TYPE: DNA
<213> ORGANISM: Zea mays

<400> SEQUENCE: 34
acgtgcatat cgccatcctc tgct                                         24

<210> SEQ ID NO 35
<211> LENGTH: 24
<212> TYPE: DNA
<213> ORGANISM: Zea mays

<400> SEQUENCE: 35
tagccacacg gtcacgtttg gacg                                         24

<210> SEQ ID NO 36
<211> LENGTH: 23
<212> TYPE: DNA
<213> ORGANISM: corn

<400> SEQUENCE: 36
cgtgcatatc gccatcctct gct                                          23

<210> SEQ ID NO 37
<211> LENGTH: 24
<212> TYPE: DNA
```

<213> ORGANISM: Zea mays

<400> SEQUENCE: 37
cagaggatgg cgatatgcac gttg                                           24

<210> SEQ ID NO 38
<211> LENGTH: 22
<212> TYPE: DNA
<213> ORGANISM: Zea mays

<400> SEQUENCE: 38
ctcaacatcc gattcaccct ca                                             22

<210> SEQ ID NO 39
<211> LENGTH: 22
<212> TYPE: DNA
<213> ORGANISM: Zea mays

<400> SEQUENCE: 39
catcgaccaa tgacattccc tc                                             22

<210> SEQ ID NO 40
<211> LENGTH: 22
<212> TYPE: DNA
<213> ORGANISM: Zea mays

<400> SEQUENCE: 40
ccttgcgcct taactatcgt gc                                             22

<210> SEQ ID NO 41
<211> LENGTH: 24
<212> TYPE: DNA
<213> ORGANISM: Zea mays

<400> SEQUENCE: 41
acccttgcgc cttaactatc gtgc                                           24

<210> SEQ ID NO 42
<211> LENGTH: 24
<212> TYPE: DNA
<213> ORGANISM: Zea mays

<400> SEQUENCE: 42
actacagtga gagtctagga aagc                                           24

<210> SEQ ID NO 43
<211> LENGTH: 24
<212> TYPE: DNA
<213> ORGANISM: Zea mays

<400> SEQUENCE: 43
agcactcgag ctttcacgcc aaca                                           24

<210> SEQ ID NO 44
<211> LENGTH: 24
<212> TYPE: DNA
<213> ORGANISM: Zea mays

<400> SEQUENCE: 44
ttggcgtgaa agctcgagtg ctcc                                           24

<210> SEQ ID NO 45
<211> LENGTH: 24

```
<212> TYPE: DNA
<213> ORGANISM: Zea mays

<400> SEQUENCE: 45
taaatggtcg tcgtattagc tgat                                        24

<210> SEQ ID NO 46
<211> LENGTH: 24
<212> TYPE: DNA
<213> ORGANISM: Zea mays

<400> SEQUENCE: 46
cagctaatac gacgaccatt tagg                                        24

<210> SEQ ID NO 47
<211> LENGTH: 23
<212> TYPE: DNA
<213> ORGANISM: Zea mays

<400> SEQUENCE: 47
tggtgtggtc gttagctact tta                                         23

<210> SEQ ID NO 48
<211> LENGTH: 24
<212> TYPE: DNA
<213> ORGANISM: Zea mays

<400> SEQUENCE: 48
aaagtagcta acgaccacac cacc                                        24

<210> SEQ ID NO 49
<211> LENGTH: 20
<212> TYPE: DNA
<213> ORGANISM: Zea mays

<400> SEQUENCE: 49
tactactact cccttctcgg                                             20

<210> SEQ ID NO 50
<211> LENGTH: 22
<212> TYPE: DNA
<213> ORGANISM: Zea mays

<400> SEQUENCE: 50
ctgatatcta tgctaattca gg                                          22

<210> SEQ ID NO 51
<211> LENGTH: 24
<212> TYPE: DNA
<213> ORGANISM: Zea mays

<400> SEQUENCE: 51
tgccgaagtg tgtcgtgaca ttgg                                        24

<210> SEQ ID NO 52
<211> LENGTH: 22
<212> TYPE: DNA
<213> ORGANISM: Zea mays

<400> SEQUENCE: 52
ctgatatcta tgctaattca gg                                          22

<210> SEQ ID NO 53
```

```
<211> LENGTH: 22
<212> TYPE: DNA
<213> ORGANISM: Zea mays

<400> SEQUENCE: 53
ccatgtaata cacagtgtcg tc                                              22

<210> SEQ ID NO 54
<211> LENGTH: 18
<212> TYPE: DNA
<213> ORGANISM: Zea mays

<400> SEQUENCE: 54
catcgtcgtg cagctggt                                                   18

<210> SEQ ID NO 55
<211> LENGTH: 22
<212> TYPE: DNA
<213> ORGANISM: Zea mays

<400> SEQUENCE: 55
cggacatttg cagttctatg gt                                              22

<210> SEQ ID NO 56
<211> LENGTH: 22
<212> TYPE: DNA
<213> ORGANISM: Zea mays

<400> SEQUENCE: 56
tacacagtgt cgtcctcttc gt                                              22

<210> SEQ ID NO 57
<211> LENGTH: 22
<212> TYPE: DNA
<213> ORGANISM: Zea mays

<400> SEQUENCE: 57
gacatttgca gttctatggt gt                                              22

<210> SEQ ID NO 58
<211> LENGTH: 22
<212> TYPE: DNA
<213> ORGANISM: Zea mays

<400> SEQUENCE: 58
cgaggtacca actaacatcg gt                                              22

<210> SEQ ID NO 59
<211> LENGTH: 22
<212> TYPE: DNA
<213> ORGANISM: Zea mays

<400> SEQUENCE: 59
atgccaaagg taccgatgtt ag                                              22

<210> SEQ ID NO 60
<211> LENGTH: 22
<212> TYPE: DNA
<213> ORGANISM: Zea mays

<400> SEQUENCE: 60
cgtcgtgcag ctggtcaccg gt                                              22
```

<210> SEQ ID NO 61
<211> LENGTH: 21
<212> TYPE: DNA
<213> ORGANISM: Zea mays

<400> SEQUENCE: 61
ctgtgatgta aagcccaga c					21

<210> SEQ ID NO 62
<211> LENGTH: 21
<212> TYPE: DNA
<213> ORGANISM: Zea mays

<400> SEQUENCE: 62
caaatgagtc atcgaagctg t					21

<210> SEQ ID NO 63
<211> LENGTH: 21
<212> TYPE: DNA
<213> ORGANISM: Zea mays

<400> SEQUENCE: 63
tagatcactc gggtcgccac a					21

<210> SEQ ID NO 64
<211> LENGTH: 21
<212> TYPE: DNA
<213> ORGANISM: Zea mays

<400> SEQUENCE: 64
gcatatatgt gatgaagacc g					21

<210> SEQ ID NO 65
<211> LENGTH: 21
<212> TYPE: DNA
<213> ORGANISM: Zea mays

<400> SEQUENCE: 65
cgaattgatt ccacccattc c					21

<210> SEQ ID NO 66
<211> LENGTH: 21
<212> TYPE: DNA
<213> ORGANISM: Zea mays

<400> SEQUENCE: 66
tggtcataca ctagataggg c					21

<210> SEQ ID NO 67
<211> LENGTH: 21
<212> TYPE: DNA
<213> ORGANISM: Zea mays

<400> SEQUENCE: 67
cctatctagt gtatgaccaa t					21

<210> SEQ ID NO 68
<211> LENGTH: 21
<212> TYPE: DNA
<213> ORGANISM: Zea mays

<400> SEQUENCE: 68
gaacagtgat tttatgagca a					21

```
<210> SEQ ID NO 69
<211> LENGTH: 21
<212> TYPE: DNA
<213> ORGANISM: Zea mays

<400> SEQUENCE: 69
gctcataaaa tcactgttca t                                              21

<210> SEQ ID NO 70
<211> LENGTH: 23
<212> TYPE: DNA
<213> ORGANISM: Zea mays

<400> SEQUENCE: 70
catgcactgg tgagtcactg ttg                                            23

<210> SEQ ID NO 71
<211> LENGTH: 23
<212> TYPE: DNA
<213> ORGANISM: Zea mays

<400> SEQUENCE: 71
agctatcgat tccctaagtg cca                                            23

<210> SEQ ID NO 72
<211> LENGTH: 23
<212> TYPE: DNA
<213> ORGANISM: Zea mays

<400> SEQUENCE: 72
ggcctccctt ccctatggta gcc                                            23

<210> SEQ ID NO 73
<211> LENGTH: 24
<212> TYPE: DNA
<213> ORGANISM: Zea mays

<400> SEQUENCE: 73
aagctatcga ttccctaagt gcca                                           24

<210> SEQ ID NO 74
<211> LENGTH: 18
<212> TYPE: DNA
<213> ORGANISM: Zea mays

<400> SEQUENCE: 74
aggcctccct tccctatg                                                  18

<210> SEQ ID NO 75
<211> LENGTH: 24
<212> TYPE: DNA
<213> ORGANISM: Zea mays

<400> SEQUENCE: 75
acagtgactc accagtgcat gcac                                           24

<210> SEQ ID NO 76
<211> LENGTH: 21
<212> TYPE: DNA
<213> ORGANISM: Zea mays

<400> SEQUENCE: 76
acagtgactc accagtgcat g                                              21
```

<210> SEQ ID NO 77
<211> LENGTH: 23
<212> TYPE: DNA
<213> ORGANISM: Zea mays

<400> SEQUENCE: 77
aaggcaagaa ggtgcttgtt gtc                                    23

<210> SEQ ID NO 78
<211> LENGTH: 24
<212> TYPE: DNA
<213> ORGANISM: Zea mays

<400> SEQUENCE: 78
gcatgcactg gtgagtcact gttg                                   24

<210> SEQ ID NO 79
<211> LENGTH: 25
<212> TYPE: DNA
<213> ORGANISM: Zea mays

<400> SEQUENCE: 79
caaggcaaga aggtgcttgt tgtcc                                  25

<210> SEQ ID NO 80
<211> LENGTH: 22
<212> TYPE: DNA
<213> ORGANISM: Zea mays

<400> SEQUENCE: 80
catcaacgac tacaacggtg aa                                     22

<210> SEQ ID NO 81
<211> LENGTH: 24
<212> TYPE: DNA
<213> ORGANISM: Zea mays

<400> SEQUENCE: 81
accatcaacg actacaacgg tgaa                                   24

<210> SEQ ID NO 82
<211> LENGTH: 24
<212> TYPE: DNA
<213> ORGANISM: Zea mays

<400> SEQUENCE: 82
aggcctccct tccctatggt agcc                                   24

<210> SEQ ID NO 83
<211> LENGTH: 18
<212> TYPE: DNA
<213> ORGANISM: Zea mays

<400> SEQUENCE: 83
caaggcaaga aggtgctt                                          18

<210> SEQ ID NO 84
<211> LENGTH: 18
<212> TYPE: DNA
<213> ORGANISM: Zea mays

<400> SEQUENCE: 84
aagaaggtgc ttgttgtc                                              18

<210> SEQ ID NO 85
<211> LENGTH: 23
<212> TYPE: DNA
<213> ORGANISM: Zea mays

<400> SEQUENCE: 85
caaggcaaga aggtgcttgt tgt                                        23

<210> SEQ ID NO 86
<211> LENGTH: 24
<212> TYPE: DNA
<213> ORGANISM: Zea mays

<400> SEQUENCE: 86
caaggcaaga aggtgcttgt tgtc                                       24

<210> SEQ ID NO 87
<211> LENGTH: 24
<212> TYPE: DNA
<213> ORGANISM: Zea mays

<400> SEQUENCE: 87
accaaggatg tcgtcaccac caat                                       24

<210> SEQ ID NO 88
<211> LENGTH: 24
<212> TYPE: DNA
<213> ORGANISM: Zea mays

<400> SEQUENCE: 88
tcacgcagtg gaaacttgat gtca                                       24

<210> SEQ ID NO 89
<211> LENGTH: 23
<212> TYPE: DNA
<213> ORGANISM: Zea mays

<400> SEQUENCE: 89
tcacgcagtg gaaacttgat gtc                                        23

<210> SEQ ID NO 90
<211> LENGTH: 22
<212> TYPE: DNA
<213> ORGANISM: Zea mays

<400> SEQUENCE: 90
cagccagcat agaagttatc ac                                         22

<210> SEQ ID NO 91
<211> LENGTH: 23
<212> TYPE: DNA
<213> ORGANISM: Zea mays

<400> SEQUENCE: 91
cacgcagtgg aaacttgatg tca                                        23

<210> SEQ ID NO 92
<211> LENGTH: 24
<212> TYPE: DNA
<213> ORGANISM: Zea mays

<400> SEQUENCE: 92

```
atctattctt ttcttcaact agca                                              24
```

<210> SEQ ID NO 93
<211> LENGTH: 1368
<212> TYPE: DNA
<213> ORGANISM: Artificial Sequence
<220> FEATURE:
<223> OTHER INFORMATION: Synthetic sequence

<400> SEQUENCE: 93

```
atgcttcatg gagcttcatc taggccagct actgccagga agtctagcgg gctcagtggc        60
accgtgcgca tccctggcga taaaagtatt tcacacagga gcttcatgtt cggaggactt       120
gctagtggag agacgagaat cactggtttg cttgagggcg aagatgttat caacaccggt       180
aaggcgatgc aagcaatggg tgccagaatc cgaaaagagg gcgatacgtg gatcatcgac       240
ggtgttggta acggaggatt gctcgctccc gaagcgccac ttgactttgg gaacgcagct       300
acggggtgcc gtcttactat gggactggta ggcgtgtatg actttgactc taccttcatc       360
ggtgacgcga gcctcactaa gagaccaatg ggacgagtgc tgaatcccct gagggagatg       420
ggtgtccagg tgaaatctga ggatggtgat cgtcttccgg ttactctgcg aggccccaag       480 accccacgc caatcacgta cagggttccg atggcgtcag cacaggtcaa gtcagcggta        540
ctcctggcgg gcctcaacac acctggaatc acaaccgtga ttgaacccat catgactaga       600
gaccacacgg agaagatgtt gcagggtttc ggcgctaatc taacggtcga aaccgacgcc       660
gacggcgtga ggacaatccg cttggagggc agaggtaaac tgactggcca agtcatcgat       720
gtgcctggag atccctcgtc cacagcgttt cccctcgtag ctgcgttgct cgtccctgga       780
tctgatgtga cgatcctgaa tgtcctcatg aatccaacta gaaccggcct catcctcaca       840
ttgcaggaga tgggtgctga catcgaggtt atcaatccta ggttggcagg tggagaggat       900
gtggccgatc tgcgcgtgcg ttctagtaca ctcaaaggcg tgaccgtccc tgaggatcgc       960
gctccatcca tgatcgacga gtacccatt ctcgccgttg ctgctgcgtt tgccgagggc       1020
gcaactgtaa tgaacggcct tgaggagttg agggttaagg agagtgacag gctgtccgcg      1080
gtggcgaatg gcctgaagct aaacggcgtg gactgcgacg aaggtgaaac gtcccttgta      1140
gtccgtggtc gcccagacgg gaaggggttg gggaatgctt cgggagctgc tgtggcgacg      1200
caccttgatc atagaatcgc catgtcattt ctggtgatgg gacttgtctc cgagaatccg      1260
gtgaccgttg acgatgctac catgatcgcc acctccttc ctgagttcat ggacctcatg       1320
gcaggcttgg gggccaagat cgagctgtct gatactaagg ccgcttga                   1368
```